(12) United States Patent
Hayashi

(10) Patent No.: US 11,230,014 B2
(45) Date of Patent: Jan. 25, 2022

(54) AUTONOMOUSLY ACTING ROBOT AND COMPUTER PROGRAM

(71) Applicant: GROOVE X, Inc., Tokyo (JP)

(72) Inventor: Kaname Hayashi, Tokyo (JP)

(73) Assignee: GROOVE X, INC., Tokyo (JP)

( * ) Notice: Subject to any disclaimer, the term of this patent is extended or adjusted under 35 U.S.C. 154(b) by 559 days.

(21) Appl. No.: 16/190,130

(22) Filed: Nov. 13, 2018

(65) Prior Publication Data
US 2019/0077021 A1 Mar. 14, 2019

Related U.S. Application Data

(63) Continuation of application No. PCT/JP2017/015525, filed on Apr. 18, 2017.

(30) Foreign Application Priority Data

May 20, 2016 (JP) .............................. JP2016-101681

(51) Int. Cl.
*B25J 9/16* (2006.01)
*A61B 5/01* (2006.01)
(Continued)

(52) U.S. Cl.
CPC ............... *B25J 9/1694* (2013.01); *A61B 5/01* (2013.01); *A61B 5/6896* (2013.01);
(Continued)

(58) Field of Classification Search
CPC ... B25J 9/1694; B25J 9/163; B25J 5/00; B25J 13/08; G01K 13/20; A61B 5/6896;
(Continued)

(56) References Cited

U.S. PATENT DOCUMENTS 7,099,742 B2 * 8/2006 Tajima ................... G06N 3/008
318/568.1
8,376,803 B2 * 2/2013 Oonaka .................. G05D 1/021
446/175
(Continued)

FOREIGN PATENT DOCUMENTS

JP 2001-246580 A 9/2001
JP 2001246580 A * 9/2001
(Continued)

OTHER PUBLICATIONS

Written Opinion of the ISA in PCT/JP2017/015525, dated Aug. 1, 2017, 16pp.
(Continued)

*Primary Examiner* — Jaime Figueroa
(74) *Attorney, Agent, or Firm* — Hauptman Ham, LLP

(57) ABSTRACT

An aspect of the invention relates to a robot including an operation determining unit that selects an operation of the robot, a drive mechanism that executes the operation selected by the operation determining unit, a body temperature detecting unit that detects a basic body temperature of a user, and a physical condition determining unit that determines a physical condition of the user based on a basic body temperature cycle of the user. When the basic body temperature of the user reaches a predetermined consideration timing in the basic body temperature cycle, the robot changes an amount of activity thereof.

20 Claims, 10 Drawing Sheets

(51) Int. Cl.
*A61B 5/00* (2006.01)
*A61B 10/00* (2006.01)
*G01K 13/20* (2021.01)

(52) U.S. Cl.
CPC ........... *A61B 10/0012* (2013.01); *B25J 9/163* (2013.01); *G01K 13/20* (2021.01); *A61B 2010/0019* (2013.01)

(58) Field of Classification Search
CPC .................. A61B 10/0012; A61B 5/01; A61B 2010/0019; A61B 10/00
USPC ........................................................ 700/253
See application file for complete search history.

(56) References Cited

U.S. PATENT DOCUMENTS

| | | | | |
|---|---|---|---|---|
| 8,909,370 | B2* | 12/2014 | Stiehl | B25J 13/081 700/245 |
| 9,814,993 | B2* | 11/2017 | Ponomarev | A63H 3/36 |
| 2003/0109959 | A1* | 6/2003 | Tajima | G06N 3/008 700/245 |
| 2005/0215171 | A1* | 9/2005 | Oonaka | A61B 5/01 446/301 |
| 2006/0100880 | A1 | 5/2006 | Yamamoto et al. | |
| 2009/0055019 | A1* | 2/2009 | Stiehl | B25J 9/1656 700/249 |
| 2010/0298976 | A1* | 11/2010 | Sugihara | A63H 11/20 700/248 |
| 2011/0118870 | A1* | 5/2011 | Sugihara | G06N 3/008 700/245 |
| 2013/0123658 | A1* | 5/2013 | OOnaka | G05D 1/021 600/549 |
| 2015/0133025 | A1* | 5/2015 | Ponomarev | A63H 3/36 446/484 |
| 2016/0193733 | A1* | 7/2016 | Abdullah | A61B 5/14532 700/240 |
| 2017/0266812 | A1* | 9/2017 | Thapliya | B25J 11/0005 |
| 2018/0241582 | A1* | 8/2018 | Nishimura | H04L 12/282 |

FOREIGN PATENT DOCUMENTS

| | | |
|---|---|---|
| JP | 2002-127059 A | 5/2002 |
| JP | 2005-305631 A | 11/2005 |
| JP | 2006-39760 A | 2/2006 |
| JP | 2011-115936 A | 6/2011 |
| JP | 2014-145569 A | 8/2014 |
| JP | 2014-176599 A | 9/2014 |
| WO | 2004/027527 A1 | 4/2004 |

OTHER PUBLICATIONS

International Search Report in PCT/JP2017/015525, dated Aug. 1, 2017. 4pp.
Office Action in JP Application No. 2017-568467, dated May 1, 2018. 13pp.

* cited by examiner

| CONSIDERATION TIMING | SPECIFIC ACTION | SELECTION PROBABILITY (%) |
|---|---|---|
| P1 | ×1 | 4 |
| | ×2 | 7 |
| | ×3 | 2 |
| | ⋮ | ⋮ |
| | ×n | 10 |
| P2 | ×1 | 8 |
| | ×2 | 4 |
| | ×3 | 4 |
| | ⋮ | ⋮ |

| EVENT | RESPONSE ACTION | SELECTION PROBABILITY (%) | | | |
|---|---|---|---|---|---|
| | | P1 | P2 | P3 | P4 |
| E1 | Y1 | 3 | 10 | 0 | 2 |
| | Y2 | 2 | 1 | 0 | 10 |
| | Y3 | 4 | 1 | 3 | 1 |
| | ⋮ | ⋮ | ⋮ | ⋮ | ⋮ |
| | Ym | 2 | 2 | 4 | 1 |
| E2 | Y1 | 3 | 0 | 0 | 10 |
| | Y2 | 1 | 1 | 0 | 2 |
| | Y3 | 1 | 2 | 0 | 1 |
| | ⋮ | ⋮ | ⋮ | ⋮ | ⋮ |

| CHILD: MALE | | |
|---|---|---|
| PHYSICAL CONDITION | ACTION | SELECTION PROBABILITY (%) |
| C1 | Z1 | 2 |
| | Z2 | 1.2 |
| | Z3 | 3 |
| | ⋮ | ⋮ |
| | $Z_P$ | 1.2 |
| C2 | Z1 | 3.2 |
| | Z2 | 4 |
| | Z3 | 1.8 |
| | ⋮ | ⋮ |

260

AUTONOMOUSLY ACTING ROBOT AND COMPUTER PROGRAM

RELATED APPLICATIONS

The present application is a continuation of International Application No. PCT/JP2017/015525, filed Apr. 18, 2017, which claims priority from Japanese Application No. 2016-101681, filed May 20, 2016, the disclosures of which application are hereby incorporated by reference herein in their entirety.

FIELD

The present disclosure relates to a robot that autonomously selects an action in accordance with an internal state or an external environment.

BACKGROUND

A human acquires various items of information from an external environment via sensory organs, and selects an action. There are times when an action is consciously selected, and times when an action is subconsciously selected. A repeated action becomes a subconscious action in time, and a new action remains in a consciousness region.

A human believes that he or she has a will to freely select an action by him or herself, that is, a free will. That a human feels emotions of affection or enmity toward another person is because he or she believes that the other person also has a free will. A person who has free will, or at least an existence that can be supposed to have a free will, is also an existence that eases a person's sadness.

A reason a human keeps a pet is that the pet provides solace, rather than whether or not the pet is useful to the human. Exactly because a pet is an existence that to a greater or lesser degree creates an impression of having a free will, the pet can become a good companion to a human.

Meanwhile, for various reasons such as not being able to secure sufficient time to look after a pet, not having a living environment in which a pet can be kept, having an allergy, or hating the thought of being parted by death, there are many people who give up on keeping a pet. A robot that performs the role of a pet may provide people who cannot keep a pet with the kind of solace that a pet provides (refer to JP-A-2001-246580 and JP-A-2006-39760).

SUMMARY

Although robot technology has advanced swiftly in recent years, the technology has not produced a presence as a pet-like companion. The inventors believe that this is because people do not consider a robot as having a free will. A human, by observing an action such that it can only be thought that a pet has a free will, feels the existence of a free will in the pet, empathizes with the pet, and is given solace by the pet.

The inventors believe that if there were a robot that can emulate a human-like or animal-like action, in other words, a robot that can autonomously select a human-like or animal-like action, empathy toward the robot could be greatly increased.

Freewill of a pet may be expressed as a lack of inhibition or innocence, and may also be expressed as consideration toward a human. A human feels special attachment toward an existence that shows consideration toward him or her, and toward an existence that interacts with him or her with sincerity.

Originally, a robot developed with an object of being useful to a human, or in other words, improving functionality. A robot shown in JP-A-2001-246580 has a function of seeking help from an exterior when detecting an abnormality in a human body. Although this kind of robot may seem reliable, a human does not feel this kind of function to be consideration or sincerity.

Embodiments of the invention, having been contrived based on a recognition of the above description, has an object of providing action control technology for increasing empathy toward a robot.

An autonomously acting robot in an aspect of the invention includes an operation determining unit that selects an operation of the robot, a drive mechanism that executes the operation selected by the operation determining unit, a body temperature detecting unit that detects a body temperature of a user, and a physical condition determining unit that determines a physical condition of the user based on a body temperature cycle of the user.

An autonomously acting robot in another aspect of the invention includes an operation determining unit that selects an operation of the robot, a drive mechanism that executes the operation selected by the operation determining unit, and a physical condition determining unit that determines a physical condition of the user based on a menstrual cycle of the user.

An autonomously acting robot in still another aspect of the invention includes an operation determining unit that selects an operation based on a vital sign of a user, and a drive mechanism that executes the operation selected by the operation determining unit.

The operation determining unit changes a method of selecting an operation in accordance with a responsive action of the user after the selected action.

An autonomously acting robot in still another aspect of the invention includes a physical condition determining unit that determines a physical condition of a user based on a vital sign of the user, an operation determining unit that refers to an action selection table that defines a physical condition and one or more response actions that can be selected with respect to the physical condition, and selects a response action corresponding to the determined physical condition, and a drive mechanism that executes the selected response action.

An autonomously acting robot in still another aspect of the invention includes a recognizing unit that determines a category of a user, a body temperature detecting unit that detects a body temperature of the user, an operation determining unit that selects an operation of the robot, and a drive mechanism that executes the operation selected by the operation determining unit.

The operation determining unit restricts an operating speed of the robot when the user includes physical characteristics of a child, and the user is detected to have a fever.

An autonomously acting robot in still another aspect of the invention includes a physical condition determining unit that determines a physical condition of a user based on a vital sign of the user, an operation determining unit that selects an action restricting an amount of activity of the robot when it is determined by the physical condition determining unit that the user is in poor physical condition, and a drive mechanism that drives the robot in accordance with an instruction from the operation determining unit.

According to embodiments of the invention, empathy toward a robot is easily increased.

BRIEF DESCRIPTION OF THE DRAWINGS

FIG. 12 is a data structure diagram of an action selection table in a second modified example;
and
FIG. 13 is a data structure diagram of an action selection table in a third modified example.

DETAILED DESCRIPTION OF THE INVENTION

Figure 1A:
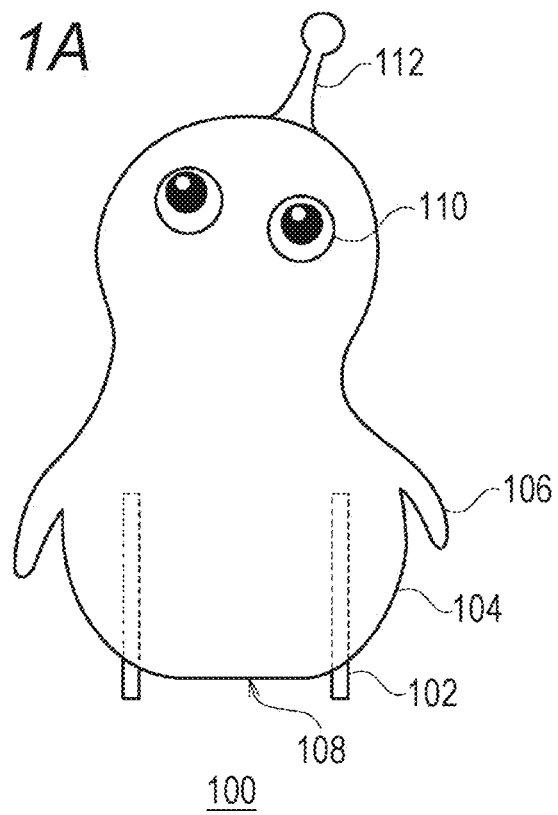
FIG. 1A is a front external view of a robot.
Figure 1B:
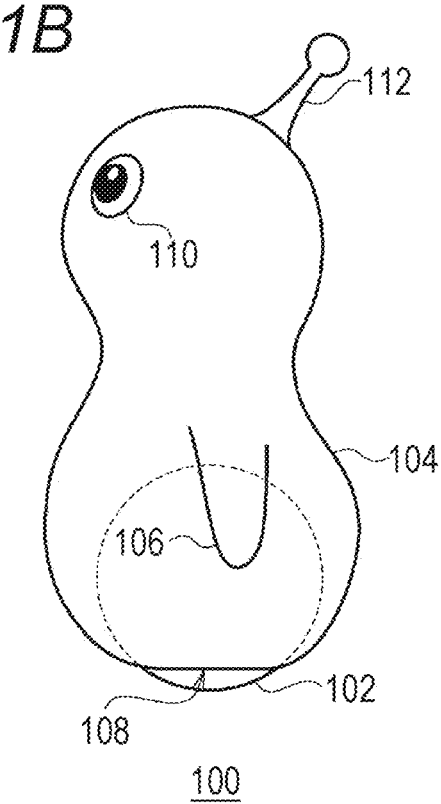
FIG. 1B is a side external view of the robot.

FIG. 1A is a front external view of a robot 100. FIG. 1B is a side external view of the robot 100.

The robot 100 in at least one embodiment is an autonomously acting robot that determines an action or gesture based on an external environment and an internal state. The external environment is recognized using various kinds of sensor, such as a camera or a thermosensor. The internal state is quantified as various parameters that express emotions of the robot 100. These will be described hereafter.

With indoor action as a precondition, the robot 100 of at least one embodiment has, for example, an interior of an owner's home as an action range. Hereafter, a human involved with the robot 100 will be called a "user", and a user forming a member of a home to which the robot 100 belongs will be called an "owner".

A body 104 of the robot 100 has a rounded form all over, and is formed of a soft material having elasticity, such as urethane, rubber, or resin. The robot 100 may be clothed. By the body 104, which is rounded, soft, and pleasant to touch, being adopted, the robot 100 provides a user with a sense of security and a pleasant tactile sensation.

A total weight of the robot 100 is 15 kilograms or less. In at least one embodiment, the total weight of the robot 100 is 10 kilograms or less. In at least one embodiment the total weight of the robot 100 is 5 kilograms or less. A majority of babies start to walk by themselves 13 months after birth. An average weight of a baby 13 months after birth is a little over 9 kilograms for boys, and a little under 9 kilograms for girls. Because of this, when the total weight of the robot 100 is 10 kilograms or less, a user can hold the robot 100 with an effort practically equivalent to that of holding a baby that cannot walk unassisted.

An average weight of a baby less than 2 months afterbirth is less than 5 kilograms for both boys and girls. Consequently, when the total weight of the robot 100 is 5 kilograms or less, a user can hold the robot 100 with an effort practically equivalent to that of holding a very young baby.

Advantages of a user holding the robot 100 easily, and wanting to hold the robot 100, are realized by the attributes of appropriate weight and roundness, softness, and pleasantness of touch. For the same reasons, a height of the robot 100 is 1.2 meters or less. In at least one embodiment, the height of the robot 100 is 0.7 meters or less.

Being able to be held is a concept of the robot 100 in at least one embodiment.

The robot 100 moves using a wheel 102. A rotational speed and a direction of rotation of two of the wheel 102 can be individually controlled. Also, the wheel 102 can also be slid upward in an interior of the body 104 of the robot 100, and completely stored in the body 104. A greater portion of the wheel 102 is hidden by the body 104 when traveling too, but when the wheel 102 is completely stored in the body 104, the robot 100 is in a state of being unable to move (hereafter called a "sitting state"). In the sitting state, a flat seating face 108 is in contact with a floor surface.

The robot 100 has two arms 106. The arms 106 do not have a function of gripping an object. The arms 106 can perform simple actions such as raising, waving, and oscillating. The two arms 106 can also be controlled individually.

A camera is incorporated in an eye 110. The eye 110 is also capable of an image display using a liquid crystal element or an organic EL element. In addition to the camera incorporated in the eye 110, various sensors, such as a highly directional microphone or an ultrasonic sensor, are mounted in the robot 100. Also, a speaker is incorporated, and the robot 100 is also capable of simple speech.

A horn 112 is attached to a head portion of the robot 100. As the robot 100 is lightweight, as heretofore described, a user can also lift up the robot 100 by grasping the horn 112.

Figure 2:
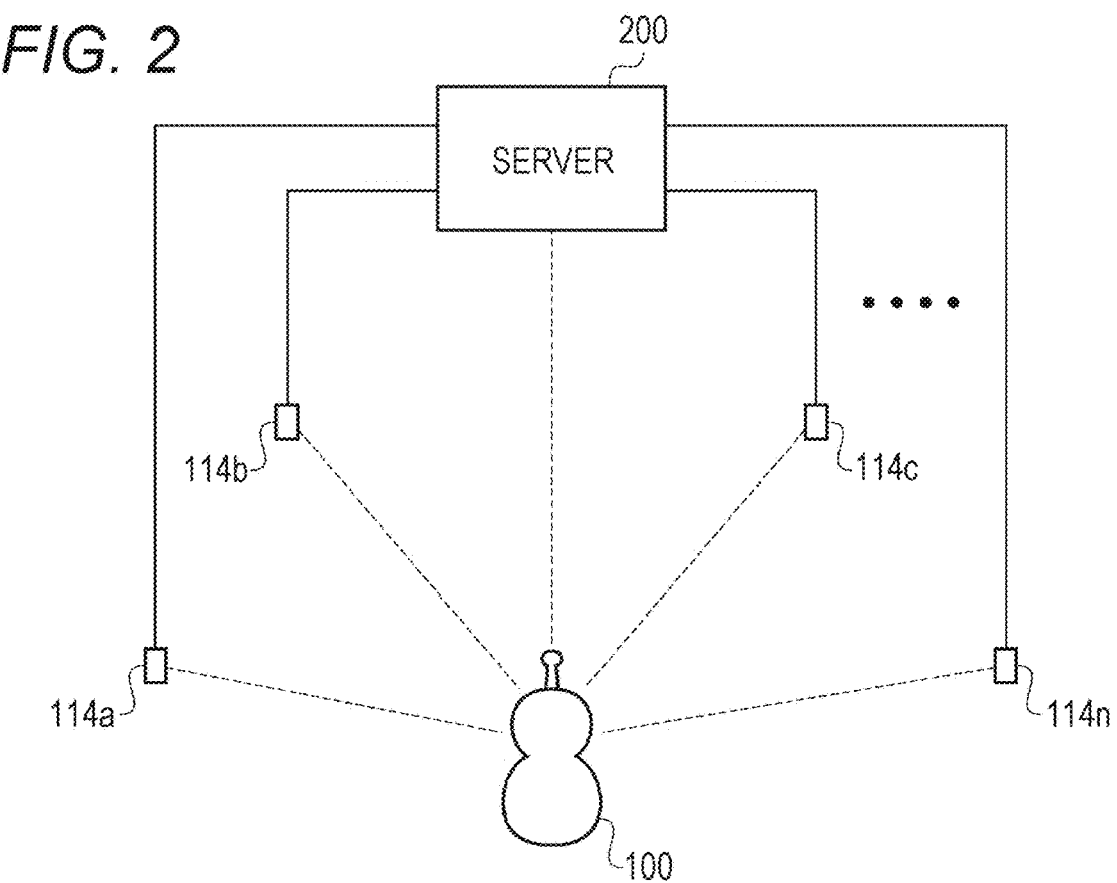
FIG. 2 is a configuration diagram of a robot system.

FIG. 2 is a configuration diagram of a robot system 300.

The robot system 300 includes the robot 100, a server 200, and a multiple of external sensors 114. The multiple of external sensors 114 (external sensors 114a, 114b, and so on to 114n) are installed in advance in a house. The external sensor 114 may be fixed to a wall surface of the house, or may be placed on a floor. Positional coordinates of the external sensor 114 are registered in the server 200. The positional coordinates are defined as x, y coordinates in the house envisaged to be an action range of the robot 100.

The server 200 is installed in the house. The server 200 and the robot 100 in at least one embodiment correspond one-to-one. The server 200 determines a basic action of the robot 100 based on information obtained from the sensors incorporated in the robot 100 and the multiple of external sensors 114.

The external sensor 114 is for reinforcing sensory components of the robot 100, and the server 200 is for reinforcing processing power of the robot 100.

The external sensor 114 regularly transmits a wireless signal (hereafter called a "robot search signal") including ID (hereafter called "beacon ID") of the external sensor 114. On receiving the robot search signal, the robot 100 returns a wireless signal (hereafter called a "robot response signal") including beacon ID. The server 200 measures a time from the external sensor 114 transmitting the robot search signal until receiving the robot response signal, and measures a distance from the external sensor 114 to the robot 100. By measuring the distance between each of the multiple of external sensors 114 and the robot 100, the server 200 identifies the positional coordinates of the robot 100.

Of course, a method whereby the robot 100 regularly transmits positional coordinates to the server 200 may also be adopted.

Figure 3:
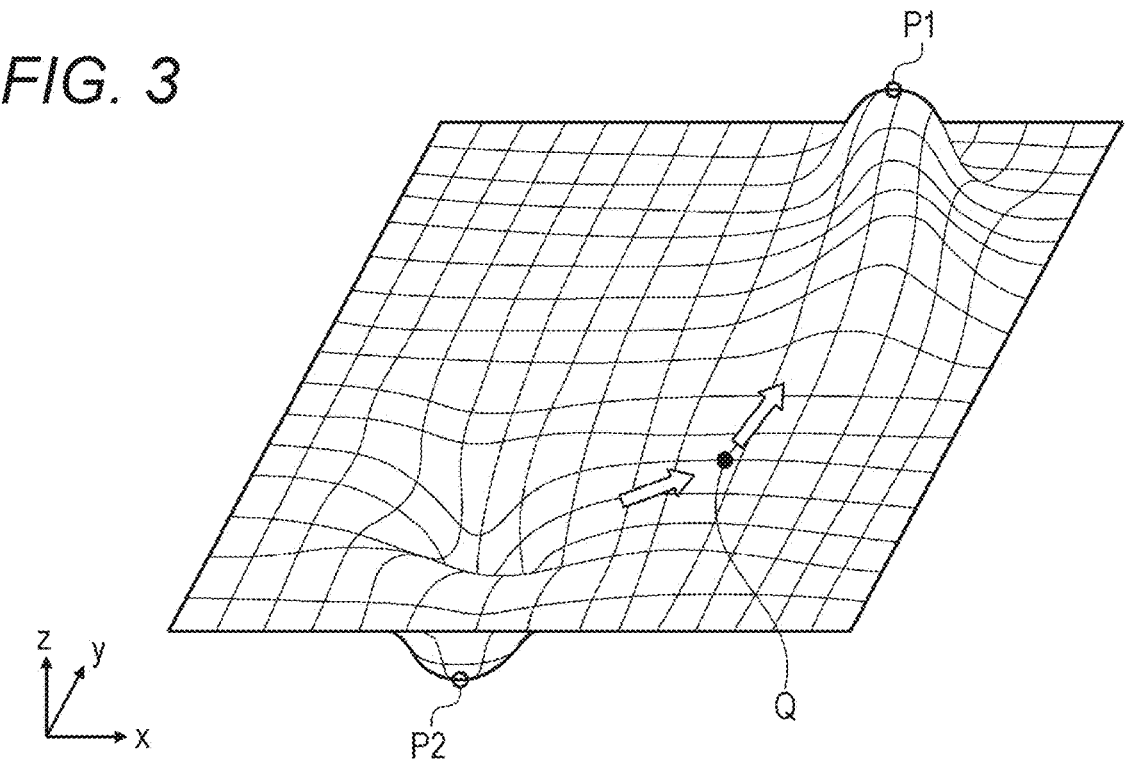
FIG. 3 is a schematic view of an emotion map.

FIG. 3 is a schematic view of an emotion map 116.

The emotion map 116 is a data table stored in the server 200. The robot 100 selects an action in accordance with the emotion map 116. The emotion map 116 shown in FIG. 3 shows a magnitude of an emotional attraction or aversion toward a place of the robot 100. An x axis and a y axis of the emotion map 116 indicate two-dimensional spatial coordinates. A z axis indicates a magnitude of an emotional attraction or aversion. When a z value is a positive value, an attraction toward the place is high, and when the z value is a negative value, the robot 100 is averse to the place.

On the emotion map 116 of FIG. 3, a coordinate P1 is a point in an indoor space managed by the server 200 as the action range of the robot 100 at which an emotion of attraction is high (hereafter called a favored point). The favored point may be a "safe place", such as behind a sofa or under a table, or may be a place in which people tend to gather or a lively place, like a living room. Also, the safe place may be a place where the robot 100 was gently stroked or touched in the past.

A definition of what kind of place the robot 100 favors is arbitrary, but the favored place is generally a place that is favored by small children, or by small animals such as dogs or cats, is set as a favored point.

A coordinate P2 is a point at which an emotion of aversion is high (hereafter called a "disliked point"). The disliked point may be a place where there is a loud noise, such as near a television, a place where there is likely to be a leak, like a bathroom or a washroom, an enclosed space or a dark place, a place where the robot 100 has been roughly treated by a user and that invokes an unpleasant memory, or the like.

A definition of what kind of place the robot 100 dislikes is also arbitrary, but the disliked place is generally a place feared by small children, or by small animals such as dogs or cats, is set as a disliked point.

A coordinate Q indicates a current position of the robot 100. The server 200 identifies position coordinates of the robot 100, using the robot search signal regularly transmitted by the multiple of external sensors 114 and the robot response signal responding to the robot search signal. For example, when the external sensor 114 with beacon ID=1 and the external sensor 114 with beacon ID=2 each detect the robot 100, the server 200 obtains the distances of the robot 100 from the two external sensors 114, and obtains the positional coordinates of the robot 100 from the distances.

In at least one embodiment, the external sensor 114 with beacon ID=1 transmits the robot search signal in a multiple of directions, and the robot 100 returns the robot response signal when receiving the robot search signal. By so doing, the server 200 may ascertain in which direction, and at what distance, the robot 100 is from which external sensor 114. Also, in at least one embodiment, the server 200 may calculate a distance moved by the robot 100 from the rotational speed of the wheel 102, thereby identifying the current position, or may identify the current position based on an image obtained from the camera.

When the emotion map 116 shown in FIG. 3 is provided, the robot 100 moves in a direction toward the favored point (coordinate P1), or in a direction away from the disliked point (coordinate P2).

The emotion map 116 changes dynamically. When the robot 100 arrives at the coordinate P1, the z value (emotion of attraction) at the coordinate P1 decreases with the passing of time. Because of this, the robot 100 can emulate animal-like behavior of arriving at the favored point (coordinate P1), "being emotionally satisfied", and in time "getting bored" with the place. In the same way, the emotion of aversion at the coordinate P2 is alleviated with the passing of time. A new favored point or disliked point appears together with the elapse of time, because of which the robot 100 carries out a new action selection. The robot 100 has "interest" in a new favored point, and ceaselessly carries out a new action selection.

The emotion map 116 expresses emotional swings as an internal state of the robot 100. The robot 100 heads for a favored point, avoids a disliked point, stays for a while at the favored point, and in time performs the next action. With this kind of control, the action selection of the robot 100 can be a human-like or animal-like action selection.

Maps that affect an action of the robot 100 (hereafter collectively called "action maps") are not limited to the type of emotion map 116 shown in FIG. 3. For example, various action maps such as curiosity, a desire to avoid fear, a desire to seek safety, and a desire to seek physical ease such as quietude, low light, coolness, or warmth, can be defined. Further, an objective point of the robot 100 may be determined by taking a weighted average of the z values of each of a multiple of action maps.

The robot 100 may also have, in addition to an action map, parameters that indicate a magnitude of various emotions or senses. For example, when a value of a sadness emotion parameter is increasing, a weighting coefficient of an action map that evaluates places in which the robot 100 feels at ease may be set high, and the value of this emotion parameter reduced by the robot 100 reaching a target point. In the same way, when a value of a parameter indicating a sense of boredom is increasing, a weighting coefficient of an action map that evaluates places in which curiosity is satisfied is set high.

Figure 4:
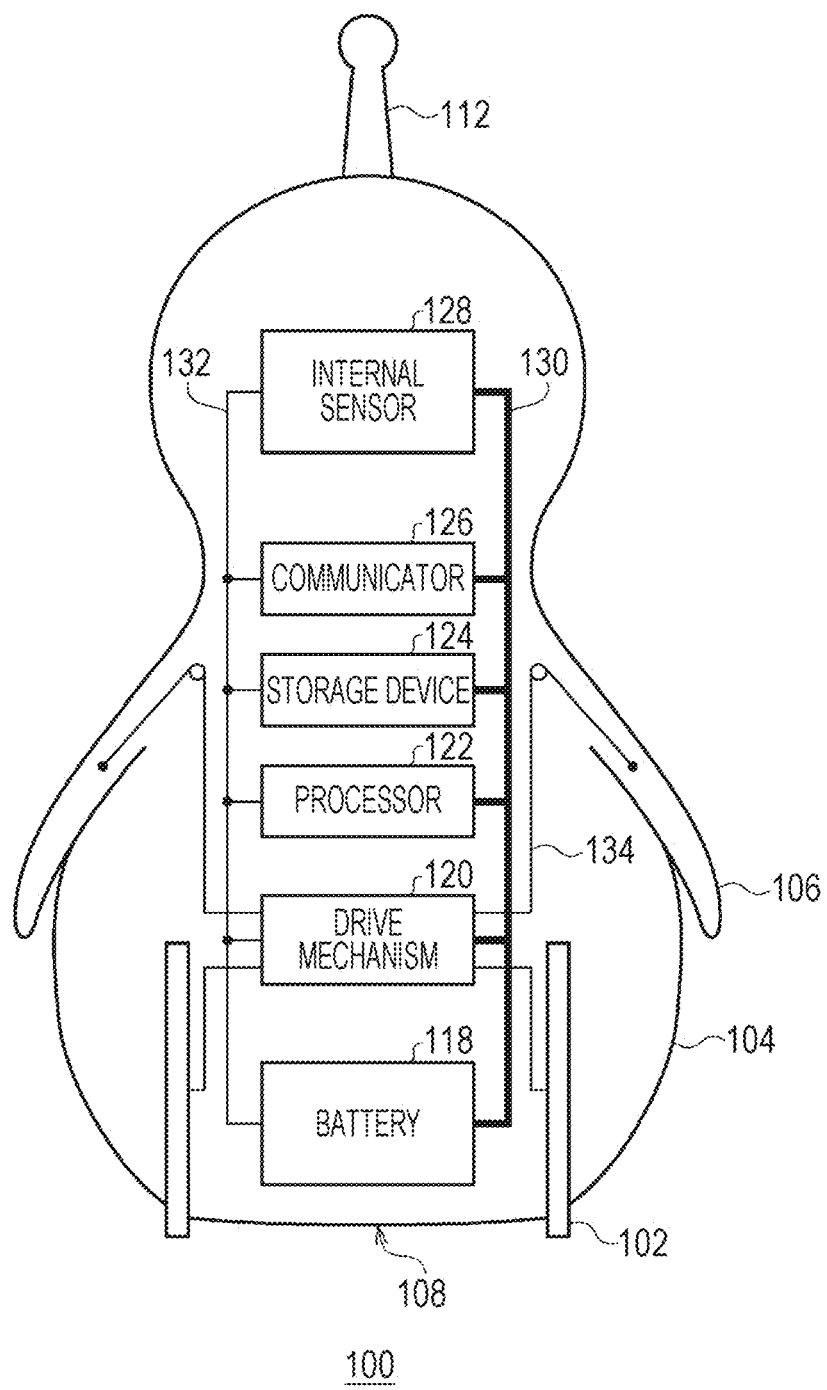
FIG. 4 is a hardware configuration diagram of the robot.

FIG. 4 is a hardware configuration diagram of the robot 100.

The robot 100 includes an internal sensor 128, a communicator 126, a storage device 124, a processor 122, a drive mechanism 120, and a battery 118. The units are connected to each other by a power line 130 and a signal line 132. The battery 118 supplies power to each unit via the power line 130. Each unit transmits and receives a control signal via the signal line 132. The battery 118 is a rechargeable battery such as a lithium ion rechargeable battery, and is a power source of the robot 100.

The internal sensor 128 is a collection of various kinds of sensor incorporated in the robot 100. Specifically, the internal sensor 128 is a camera, a highly directional microphone, an infrared sensor, a thermosensor, a touch sensor, an acceleration sensor, a smell sensor, and the like. The smell sensor is an already known sensor that applies a principle that electrical resistance changes in accordance with an adsorption of a molecule forming a source of a smell. The smell sensor classifies various smells into multiple kinds of category (hereafter called "smell categories").

The communicator 126 is a communication module that carries out wireless communication with the server 200 and various kinds of external device, such as the external sensor 114 and a mobile device possessed by a user, as a target. The storage device 124 is configured of a non-volatile memory and a volatile memory, and stores a computer program and various kinds of setting information. The processor 122 is means of executing a computer program. The drive mechanism 120 is an actuator that controls various mechanisms, such as the wheels 102 and the arms 106.

In addition to this, an indicator, a speaker, and the like are also mounted in the robot 100.

The processor 122 selects an action of the robot 100 while communicating with the server 200 or the external sensor 114 via the communicator 126. Various kinds of external information obtained by the internal sensor 128 also affect the action selection. The drive mechanism 120 mainly controls the wheel 102 and the arm 106. The drive mechanism 120 changes a direction of movement and a movement speed of the robot 100 by changing the rotational speed and the direction of rotation of each of the two wheels 102. Also, the drive mechanism 120 can also raise and lower the wheel 102. When the wheel 102 rises, the wheel 102 is completely stored in the body 104, and the robot 100 comes into contact with a floor surface via the seating face 108, taking on the sitting state.

The arm 106 can be lifted up by the drive mechanism 120 pulling the arm 106 via a wire 134. A gesture like an arm waving can also be performed by the arm 106 being caused to oscillate. A more complex gesture can also be represented by a large number of the wire 134 being utilized. That is, as the number of wires 134 in arm 106 complexity of possible gestures by arm 106 increases.

Figure 5:
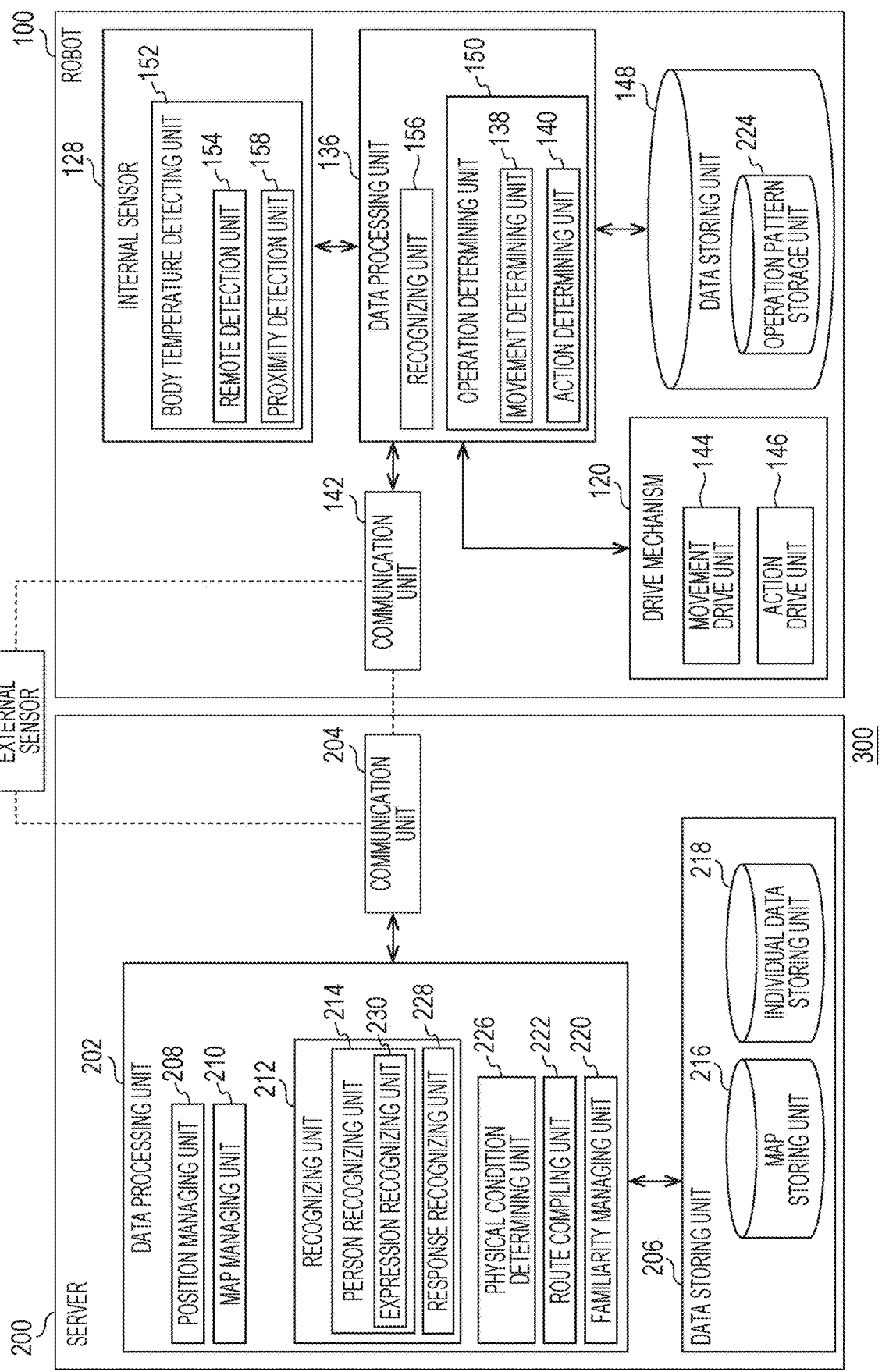
FIG. 5 is a functional block diagram of the robot system.

FIG. 5 is a functional block diagram of a robot system 300.

As heretofore described, the robot system 300 includes the robot 100, the server 200, and the multiple of external sensors 114. Each component of the robot 100 and the server 200 is realized by hardware including a computer formed of a CPU (central processing unit), various kinds of coprocessor, and the like, a storage device that is a memory or storage, and a wired or wireless communication line that links the computer and the storage device, and software that is stored in the storage device and supplies a processing command to the computer. A computer program may be configured of a device driver, an operating system, various kinds of application program positioned in an upper layer thereof, and a library that provides a common function to the programs. Each block described hereafter indicates a functional unit block rather than a hardware unit configuration.

One portion of the functions of the robot 100 may be realized by the server 200, and one portion or all of the functions of the server 200 may be realized by the robot 100.

Server 200

The server 200 includes a communication unit 204, a data processing unit 202, and a data storage unit 206. The communication unit 204 manages a process of communicating with the external sensor 114 and the robot 100. The data storage unit 206 stores various kinds of data. The data processing unit 202 executes various kinds of process based on data acquired by the communication unit 204 and data stored in the data storage unit 206. The data processing unit 202 also functions as an interface of the communication unit 204 and the data storage unit 206.

The data storage unit 206 includes a map storage unit 216 and an individual data storage unit 218. The map storage unit 216 stores a multiple of action maps. The individual data storage unit 218 stores information on a user, and in particular, on an owner. Specifically, the individual data storage unit 218 stores various kinds of parameters such as familiarity with respect to a user, and physical characteristics and behavioral characteristics of a user. The individual data storage unit 218 may also store other attribute information such as age and gender.

The robot 100 identifies a user based on the physical characteristics and the behavioral characteristics of the user. The robot 100 constantly captures a periphery using the incorporated camera. Further, the robot 100 extracts the physical characteristics and the behavioral characteristics of a person appearing in an image. The physical characteristics may be visual characteristics inherent to a body, such as a height, clothes worn by choice, a presence or absence of spectacles, a skin gloss, a hair color, or an ear size, or may also include other characteristics such as an average body temperature, a smell, or a voice quality. The behavioral characteristics, specifically, are characteristics accompanying behavior, such as a place the user favors, a briskness of movement, and a presence or absence of smoking. For example, the robot 100 extracts behavioral characteristics such that an owner identified as a father is often out of the home, and is often motionless on a sofa when at home, but a mother is often in a kitchen, and an activity range is broad.

The robot 100 clusters users appearing with a high frequency as "owners" based on physical characteristics and behavioral characteristics obtained from a large amount of image information and other sensing information.

Although a method of identifying a user from user ID is simple and reliable, the user having a device that can provide user ID is a precondition. Meanwhile, the method of identifying a user from physical characteristics or behavioral characteristics is such that an image recognition process is weighty, but there is an advantage in that even a user who does not have a mobile device can be identified. One of the two methods may be employed alone, or user identification may be carried out using the two methods together in a complementary way.

In at least one embodiment, users are clustered based on physical characteristics and behavioral characteristics, and a user is identified using deep learning (a multilayer neural network). Details will be described hereafter.

The robot 100 has a familiarity internal parameter for each user. When the robot 100 recognizes an action indicating a liking toward the robot 100, such as picking the robot 100 up or speaking to the robot 100, familiarity with respect to that user increases. Familiarity decreases with respect to a user not involved with the robot 100, a user who behaves roughly, or a user met infrequently.

The data processing unit 202 includes a position managing unit 208, a map managing unit 210, a recognizing unit 212, a physical condition determining unit 226, a route compiling unit 222, and a familiarity managing unit 220.

The position managing unit 208 identifies the positional coordinates of the robot 100 using a method described using FIG. 2. Also, the position managing unit 208 may also track positional coordinates of a user in real time.

The map managing unit 210 selects one of a multiple of action maps, and decides the direction of movement of the robot 100 based on the z value of the selected action map. The map managing unit 210 may also decide the direction of movement of the robot 100 by taking a weighted average of the z values of the multiple of action maps.

For example, it is assumed that the z values at a coordinate R1 and a coordinate R2 on an action map A are 4 and 3, and the z values at the coordinate R1 and the coordinate R2 on an action map B are −1 and 3. When taking a simple average, the total z value at the coordinate R1 is 4−1=3, and the total z value at the coordinate R2 is 3+3=6, because of which the robot 100 heads in the direction of the coordinate R2 rather than the coordinate R1.

When the action map A is weighted 5 times with respect to the action map B, the total z value at the coordinate R1 is 4×5−1=19, and the total z value at the coordinate R2 is 3×5+3=18, because of which the robot 100 heads in the direction of the coordinate R1.

The recognizing unit 212 recognizes an external environment. Various kinds of recognition, such as recognition of weather or season based on temperature and humidity, and recognition of shelter (a safe area) based on an amount of light and temperature, are included in the recognition of the external environment. The recognizing unit 212 further includes a person recognizing unit 214 and a response recognizing unit 228. The person recognizing unit 214 recognizes a person from an image filmed by the camera incorporated in the robot 100, and extracts the physical characteristics and the behavioral characteristics of the person. Further, based on the physical characteristic information and behavioral characteristic information registered in the individual data storage unit 218, the person recognizing unit 214 determines what person, such as a father, a mother, or an eldest son, the user filmed, that is, the user the robot 100 is looking at, corresponds to. The person recognizing unit 214 includes an expression recognizing unit 230. The expression recognizing unit 230 infers an emotion of a user using image recognition of an expression of the user.

In addition to a person, the person recognizing unit 214 also, for example, extracts characteristics of a cat or a dog that is a pet. Hereafter, a description will be given assuming that not only a person but also a pet is included as a user or an owner.

The response recognizing unit 228 recognizes various responsive actions performed with respect to the robot 100, and classifies the actions as pleasant or unpleasant actions (to be described hereafter). Also, the response recognizing unit 228 recognizes a responsive action of an owner with respect to an action of the robot 100, thereby classifying the responsive action as a positive or negative response (to be described hereafter).

Pleasant and unpleasant actions are distinguished depending on whether a responsive action of a user is pleasing or unpleasant for an animal. For example, being hugged is a pleasant action, and being kicked is an unpleasant action. Positive and negative responses are distinguished depending on whether a responsive action of a user indicates a pleasant emotion or an unpleasant emotion of the user. For example, being hugged is a positive response, and being kicked is a negative response.

The physical condition determining unit 226 determines a physical condition of an owner. "Physical condition" in this embodiment is a concept including both a physical state and a mental state. The physical condition determining unit 226 in this embodiment infers a physical condition of an owner from a menstrual cycle of the owner. actions (to be described hereafter).

The route compiling unit 222 compiles a route along which the robot 100 should move. The route compiling unit 222 compiles a multiple of candidate routes, and the robot 100 may select any of the routes. Route selection will be described hereafter.

The familiarity managing unit 220 manages familiarity for each user. As heretofore described, familiarity is registered as one portion of individual data in the individual data storage unit 218. Details of familiarity management will be described hereafter.

Robot 100

The robot 100 includes a communication unit 142, a data processing unit 136, a data storing unit 148, a drive mechanism 120, and an internal sensor 128. The communication unit 142 corresponds to the communicator 126 (refer to FIG. 4), and manages a process of communicating with the external sensor 114 and the server 200. The data storing unit 148 stores various kinds of data. The data storing unit 148 corresponds to the storage device 124 (refer to FIG. 4). The data processing unit 136 executes various kinds of process based on data acquired by the communication unit 142 and data stored in the data storing unit 148. The data processing unit 136 corresponds to the processor 122 and a computer program executed by the processor 122. The data processing unit 136 also functions as an interface of the communication unit 142, the internal sensor 128, the drive mechanism 120, and the data storing unit 148.

The internal sensor 128 includes a body temperature detection unit 152. The body temperature detection unit 152 measures a body temperature of a user. The body temperature detection unit 152 includes a remote detection unit 154 and a proximity detection unit 158. The remote detection unit 154 is a non-contact temperature sensor such as a radiation thermometer or thermography, and can measure the body temperature of a user, even from afar, by measuring radiant heat of the user. The proximity detection unit 158 is a contact temperature sensor such as a thermistor, bimetal, or a glass thermometer, and can measure body temperature more accurately than the remote detection unit 154 by coming into direct contact with a user.

The data storage unit 148 includes an operation pattern storage unit 224 that defines various kinds of operations of the robot 100. The operation pattern storage unit 224 stores a specific action selection table of the robot 100. Details of the specific action selection table will be described hereafter.

The data processing unit 136 includes a recognizing unit 156 and an operation determining unit 150. The operation determining unit 150 decides an operation of the robot 100. The operation determining unit 150 includes a movement determining unit 138 and an action determining unit 140.

The drive mechanism 120 includes a movement drive unit 144 and an action drive unit 146. The movement determining unit 138 decides a direction of movement of the robot 100. The movement drive unit 144 causes the robot 100 to head toward a target point by driving the wheel 102 in accordance with an instruction from the movement determining unit 138. The map managing unit 210 of the server 200 calculates a movement destination (target point) of the robot 100 in real time, based on an action map. The server 200 transmits the coordinates of the target point to the robot 100, and the movement determining unit 138 causes the robot 100 to move toward the target point.

Although an action map decides the main element of the direction of movement of the robot 100, the robot 100 can also carry out an action corresponding to familiarity.

The action determining unit 140 decides a gesture of the robot 100. Multiple gestures are defined in advance in the data storing unit 148. Specifically, a gesture of sitting by housing the wheel 102, a gesture of raising the arm 106, a gesture of causing the robot 100 to carry out a rotating action by causing the two wheels 102 to rotate in reverse or by causing only one wheel 102 to rotate, a gesture of shaking by causing the wheel 102 to rotate in a state in which the wheel 102 is housed, and the like are defined.

The action determining unit 140 can also perform a gesture of holding up both arms 106 as a gesture asking for "a hug" when a user with a high degree of familiarity is nearby, and can also perform a gesture of no longer wanting to be hugged by causing the wheel 102 to rotate in reverse in a housed state when bored of the "hug". The action drive unit 146 causes the robot 100 to perform various gestures by driving the wheel 102 and the arm 106 in accordance with an instruction from the action determining unit 140.

The recognizing unit 156 analyzes external information obtained from the internal sensor 128. The recognizing unit 156 is capable of visual recognition (a visual unit), smell recognition (an olfactory unit), sound recognition (an aural unit), and tactile recognition (a tactile unit).

The recognizing unit 156 regularly films an exterior angle using the incorporated camera (the internal sensor 128), and detects a user that is a moving object such as a person or a pet. Characteristics thereof are transmitted to the server 200, and the person recognizing unit 214 of the server 200 extracts the physical characteristics of the moving object. The recognizing unit 156 also detects a smell of the user and a voice of the user. Smell and sound (voice) are classified into multiple kinds using an already known method. Also, a temperature when touched can also be detected using the body temperature detection unit 152.

When a strong force is applied to the robot 100, the recognizing unit 156 recognizes this using an incorporated acceleration sensor, and the response recognizing unit 228 of the server 200 recognizes that a "violent action" has been performed by a user in the vicinity. When a user picks the robot 100 up by grabbing the horn 112, this may also be recognized as a violent action. When a user in a state of confronting the robot 100 speaks in a specific volume region and a specific frequency band, the response recognizing unit 228 of the server 200 may recognize that a "speaking action" has been performed with respect to the robot 100. Also, when a temperature in the region of body temperature is detected, the response recognizing unit 228 of the server 200 recognizes that a "touching action" has been performed by a user, and when upward acceleration is detected in a state in which touching is recognized, the response recognizing unit 228 of the server 200 recognizes that a "hug" has been performed. Physical contact when a user raises the body 104 may also be sensed, and a hug may also be recognized by a load acting on the wheel 102 decreasing.

In this way, the response recognizing unit 228 of the server 200 recognizes various kinds of responses by a user toward the robot 100. "Pleasant" or "unpleasant", and "positive" or "negative", are correlated to one portion of typical responsive actions among these various kinds of responsive actions. In general, almost all responsive actions that are pleasant actions are positive responses, and almost all responsive actions that are unpleasant actions are negative responses. Pleasant and unpleasant actions relate to familiarity, and positive and negative responses affect action selection of the robot 100 (to be described hereafter).

A series of recognition processes including detecting, analyzing, and determining may be carried out by the recognizing unit 212 of the server 200 alone, or carried out by the recognizing unit 156 of the robot 100 alone, or the two may execute the recognition processes while dividing roles.

The familiarity managing unit 220 of the server 200 changes the familiarity toward a user in accordance with a responsive action recognized by the recognizing unit 156. Essentially, the familiarity toward a user who carries out a pleasant action increases, while the familiarity toward a user who carries out an unpleasant action decreases.

The recognizing unit 212 of the server 200 may determine whether a response is pleasant or unpleasant, and the map managing unit 210 may change the z value of the point at which the pleasant or unpleasant action has been carried out on an action map that represents "affection toward a place". For example, when a pleasant action is carried out in a living room, the map managing unit 210 may set a favored point at a high probability in the living room. In this case, a positive feedback advantage is realized in that the robot 100 favors the living room, and further favors the living room due to being the recipient of a pleasant action in the living room.

The route compiling unit 222 of the server 200 compiles as needed a movement route (hereafter called an "escape route") assuming a case in which an unknown person, that is, a moving object with low familiarity, is detected (hereafter called an "escape event"), with the current position of the robot 100 as an origin. In order to decide an escape route, at least (1) a selection of a final movement position (hereafter called a "movement ending position") and (2) a position from which movement is to be started (hereafter called a "movement starting position") are needed. When the movement ending position is sought, a route from the movement starting position to the movement ending position compiled, and a shift made to actual action, after the robot 100 detects an unknown person, time taken until action increases. Because of this, an escape action that should by rights be an immediate action becomes unnatural.

The route compiling unit 222 compiles as needed an escape route in accordance with the current position of the robot 100, even when no escape event has occurred. When an escape event occurs, the robot 100 can immediately take evasive action based on an escape route compiled in advance by the route compiling unit 222. It is sufficient that the movement starting position is the current position of the robot 100. The movement ending position may be an arbitrary position separated by a predetermined distance from the robot 100, or may be set in a vicinity of a user whose familiarity is of a predetermined value or greater.

The function of the route compiling unit 222 may be mounted in the robot 100 rather than in the server 200.

The map managing unit 210 compiles a map (hereafter called a "static map") recording a safe place, such as a position of furniture behind which the robot 100 can hide or a safe place, existing in a space in which the robot 100 exists, and stores the map in the map storage unit 216. Also, the map managing unit 210 compiles a map (hereafter called a "dynamic map") recording a position of a person with high familiarity who is in the space in which the robot 100 exists (normally in the same house), and stores the map in the map storage unit 216. The route compiling unit 222 may utilize the dynamic map with priority over the static map. Because of this, the robot 100 can prioritize an evasive action of hiding behind a person over hiding behind an object when an escape event occurs.

The route compiling unit 222 refers to the static map and the dynamic map saved in the map storage unit 216, and adopts a point nearest to the current position of the robot 100 as the movement ending position. Further, the route compiling unit 222 compiles as needed an escape route from the movement starting position to the movement ending position. The route compiling unit 222 may compile an escape route every time the robot 100 moves, or may compile an escape route regularly.

The person recognizing unit 214 of the server 200 detects a moving object from various kinds of data obtained from the external sensor 114 or the internal sensor 128, and extracts characteristics (physical characteristics and behavioral characteristics) thereof. Further, the person recognizing unit 214 cluster analyzes multiple moving objects based on these characteristics. Not only a human, but also a pet such as a dog or cat, may be a target of analysis as a moving object.

For example, the robot 100 regularly carries out image capturing, and the person recognizing unit 214 recognizes a moving object from the images, and extracts characteristics of the moving object. When a moving object is detected, physical characteristics and behavioral characteristics are also extracted from the smell sensor, the incorporated highly directional microphone, the temperature sensor, and the like. For example, when a moving object appears in an image, various characteristics are extracted, such as having a beard, being active early in the morning, wearing red clothing, smelling of perfume, having a loud voice, wearing spectacles, wearing a skirt, having gray hair, being tall, being plump, being suntanned, or being on a sofa.

When a moving object (user) having a beard is often active early in the morning (gets up early) and rarely wears red clothing, a first profile that is a cluster (user) that gets up early, has a beard, and does not often wear red clothing is created. Meanwhile, when a moving object wearing spectacles often wears a skirt, but the moving object does not have a beard, a second profile that is a cluster (user) that wears spectacles and wears a skirt, but definitely does not have a beard, is created.

Although the above is a simple example, the first profile corresponding to a father and the second profile corresponding to a mother are formed using the heretofore described method, and the robot 100 recognizes that there are at least two users (owners) in this house.

Note that the robot 100 does not need to recognize that the first profile is the "father". In all cases, it is sufficient that the robot 100 can recognize a figure that is "a cluster that has a beard, often gets up early, and hardly ever wears red clothing".

It is assumed that the robot 100 newly recognizes a moving object (user) in a state in which this kind of cluster analysis is completed.

At this time, the person recognizing unit 214 of the server 200 extracts characteristics from sensing information of an image or the like obtained from the robot 100, and determines which cluster a moving object near the robot 100 corresponds to using deep learning (a multilayer neural network). For example, when a moving object that has a beard is detected, the probability of the moving object being the father is high. When the moving object is active early in the morning, it is still more certain that the moving object corresponds to the father. Meanwhile, when a moving object that wears spectacles is detected, there is a possibility of the moving object being the mother. When the moving object has a beard, the moving object is neither the mother nor the father, because of which the person recognizing unit 214 determines that the moving object is a new person who has not been cluster analyzed.

Formation of a cluster by characteristic extraction (cluster analysis) and application to a cluster accompanying characteristic extraction (deep learning) may be executed concurrently.

Familiarity toward a moving object (user) changes in accordance with how the robot 100 is treated by the user.

The familiarity managing unit 220 increases or reduces familiarity toward each clustered user. Familiarity mainly changes in accordance with (1) detection (visual recognition), (2) physical contact, and (3) speaking.

1. Detection

When a small child is detected in an image filmed by the robot 100, the small child is "visually recognized" by the robot 100. More specifically, when it is determined that the characteristics of the detected moving object correspond with the cluster (profile) of the small child, using deep learning based on characteristic information obtained from the filmed image and other characteristic information obtained from the smell sensor and the like when filming, it is determined that there is visual recognition. When it is determined that there is visual recognition, the familiarity managing unit 220 increases the familiarity of the small child. The more frequently a user is detected, the more liable the familiarity is to increase.

According to this kind of control method, the robot 100 emulates animal-like behavior in being more liable to feel a sense of closeness toward a person frequently met.

Not being limited to simple detection, familiarity may also increase when "eyes meet". The recognizing unit 156 of the robot 100 may recognize a facial image of a confronting user, recognize a line of sight from the facial image, and recognize that "eyes have met" when the time for which the line of sight is directed toward the robot 100 is a predetermined time or greater.

2. Physical Contact

When the robot 100 visually recognizes a user, and detects a touch (physical contact) from the user, it is determined that interest in the robot 100 has been shown by the user, and familiarity increases. For example, when the robot 100 is touched by the mother, the familiarity managing unit 220 increases the familiarity of the mother. The robot 100 may detect a touching of the robot 100 by an outer shell being covered with a piezoelectric fabric. Touching may also be detected by the body temperature of the user being detected by the temperature sensor. When the robot 100 detects a hug, familiarity may be considerably increased on the basis that strong affection toward the robot 100 has been shown.

Meanwhile, when the robot 100 detects a violent action such as being kicked, being hit, or having the horn 112 grasped, the familiarity managing unit 220 reduces familiarity. For example, when the robot 100 is thrown by the small child, the familiarity managing unit 220 considerably reduces familiarity with respect to the small child.

According to this kind of control method, the robot 100 emulates animal-like behavior in being more liable to feel a sense of closeness toward a person who touches the robot 100 gently, but to dislike a violent person.

3. Speaking

Familiarity is also changed when the robot 100 detects speech directed toward the robot 100. For example, familiarity is increased when the robot 100 detects the name of the robot 100 or an affectionate term in a predetermined volume range. Typical terminological patterns such as "you're cute", "you're funny", or "come here" may be registered in advance as affectionate terms, and whether or not a term is an affectionate term may be determined using speech recognition. Meanwhile, familiarity may be reduced when the robot 100 is spoken to at a high volume exceeding a normal volume range. For example, familiarity is reduced when the robot 100 is scolded in a loud voice, or when surprised.

Also, familiarity may be reduced when an abusive term is directed at the robot 100. Typical terminological patterns such as "stop it", "stay away", "get away", or "idiot" may be registered in advance as abusive terms, and whether or not a term is an abusive term may be determined using speech recognition.

The name of the robot 100 may be registered in advance by a user. Alternatively, the robot 100 may recognize a term used with particular frequency among various terms directed at the robot 100 as being the name of the robot 100. In this case, terms generally liable to be used frequently, such as "hey" and "come here", may be eliminated from candidates for name recognition.

According to the heretofore described control method, the robot 100 sets a high familiarity for a frequently met person, a person who frequently touches the robot 100, and a person who frequently speaks to the robot 100. Meanwhile, familiarity decreases for a rarely seen person, a person who does not often touch the robot 100, a violent person, and a person who scolds in a loud voice. The robot 100 changes the familiarity of each user based on various items of outside environment information detected by the sensors (visual, tactile, and aural).

The familiarity managing unit 220 reduces familiarity with the passing of time. For example, the familiarity managing unit 220 may reduce the familiarity of all users by 1 each every 10 minutes. When a user does not continue to be involved with the robot 100, or in other words, when a user does not continue to treat the robot 100 kindly, the user cannot maintain an intimate relationship with the robot 100.

The actual robot 100 autonomously carries out a complex action selection in accordance with an action map. The robot 100 acts while being affected by a multiple of action maps based on various parameters such as loneliness, boredom, and curiosity. When the effect of the action maps is removed, or when in an internal state in which the effect of the action maps is small, the robot 100 essentially attempts to approach a person with high familiarity, and attempts to move away from a person with low familiarity.

Actions of the robot 100 are classified below in accordance with familiarity.

1. A Cluster with Extremely High Familiarity

The robot 100 strongly expresses a feeling of affection by approaching a user (hereafter called an approaching action), and performing an affectionate gesture defined in advance as a gesture indicating goodwill toward a person.

2. A Cluster with Comparatively High Familiarity

The robot 100 carries out only an approaching action.

3. A Cluster with Comparatively Low Familiarity

The robot 100 does not carry out any special action.

4. A Cluster with Particularly Low Familiarity

The robot 100 carries out a withdrawing action.

According to the heretofore described control method, the robot 100 approaches the user when finding a user with high familiarity, and conversely, moves away from the user when finding a user with low familiarity. According to this kind of control method, the robot 100 can express by behavior a so-called "shyness". Also, when a visitor (a user A with low familiarity) appears, the robot 100 may move away from the visitor and head toward a family member (a user B with high familiarity). In this case, the user B can perceive that the robot 100 is shy and feeling uneasy, and relying on the user B. Owing to this kind of behavioral expression, pleasure at being chosen and relied upon, and an accompanying feeling of affection, are evoked in the user B.

Meanwhile, when the user A, who is a visitor, visits frequently, and speaks to and touches the robot 100, familiarity of the robot 100 toward the user A gradually rises, and the robot 100 ceases to perform an action of shyness (a withdrawing action) with respect to the user A. The user A can also feel affection toward the robot 100 by perceiving that the robot 100 has become accustomed to the user A.

The heretofore described action selection need not necessarily be executed constantly. For example, when an internal parameter indicating curiosity of the robot 100 is high, weight is given to an action map from which a place in which the curiosity is satisfied is obtained, because of which there is also a possibility that the robot 100 does not select an action affected by familiarity. Also, when the external sensor 114 installed in the hall detects the return home of a user, the robot 100 may execute an action of greeting the user with maximum priority.

Consideration Function Based on Menstrual Cycle

Figure 6:
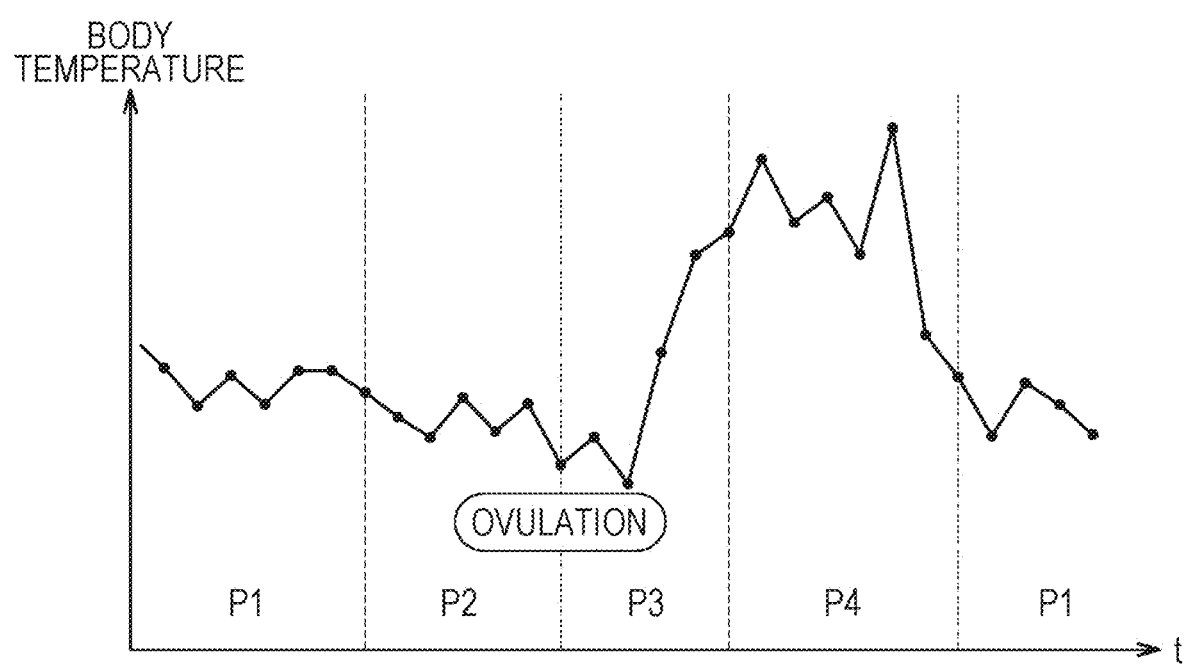
FIG. 6 is a graph showing a basic body temperature cycle of a female.

FIG. 6 is a graph showing a basic body temperature cycle of a female.

The robot 100 in this embodiment autonomously changes behavior in accordance with the physical condition of a female owner. A basic body temperature cycle is one vital sign useful for determining the physical condition of a female. In connection with FIG. 6, firstly, a general theory on a relationship between a basic body temperature cycle and a mental state of a female will be described.

It is assumed that a menstrual cycle is such that approximately four weeks (around 28 days) constitute one cycle. The menstrual cycle is broadly divided into the following states P1 to P4.

1. State P1 (menstruation): secretion of progesterone, which raises body temperature, decreases, because of which the body cools, and blood circulation worsens. The female is liable to be highly strung, and easily depressed. The skin is liable to become rough.
2. State P2 (the one week until ovulation): balance of the autonomous nerve improves, and the female is mentally stable. Blood circulation also improves, and the skin becomes tight and glossy.
3. State P3 (the one week after ovulation): swelling, constipation, shoulder stiffness, and the like are likely to occur. The sympathetic nerves become active, and emotional fluctuations are likely to increase.
4. State P4 (before menstruation): swelling, constipation, shoulder stiffness, and the like are particularly likely to occur. The female is liable to become irritable and uneasy due to abrupt fluctuations in hormone balance. Skin troubles such as pimples and roughness are also likely to occur.

The robot 100 regularly measures the body temperature of a female owner using the body temperature detecting unit 152. The measured body temperature is sent to the physical condition determining unit 226 of the server 200, and the physical condition determining unit 226 records the body temperature in the individual data storage unit 218. When a multiple of female owners exist, a body temperature cycle is recorded for each female owner. The physical condition determining unit 226 determines which of the heretofore described four states P1 to P4 a female owner is in based on the body temperature cycle of the female owner, or more specifically, a cycle of basic body temperature measured at a time of repose and the measured basic body temperature.

For example, the physical condition determining unit 226 calculates an average value, a standard deviation, and the like of the basic body temperature of a female owner, and may determine that the state of the female owner has shifted from the state P4 to the state P1 when the basic body temperature (measurement value) is lower than a lower limit body temperature lower by "standard deviation×n" than the average value of the basic body temperature.

Not being limited to an absolute value of basic body temperature, the physical condition determining unit 226 may determine a state shift based on a rate of change in basic body temperature. When the basic body temperature rises by x % per day, the physical condition determining unit 226 may determine that the state of the female owner has shifted from the state P2 to the state P3.

By managing the basic body temperature cycle of each female owner, the next menstrual cycle, and the like, can be predicted. When four weeks elapse from the state of the female owner shifting from the state P2 to the state P3, it can be predicted that the timing of a state shift from the state P2 to the state P3 is near. In the same way, when 1.5 weeks elapse from the state of the female owner shifting to the state P1, it can be determined uniformly that the state of the female owner has shifted to the state P2, regardless of the basic body temperature.

The physical condition determining unit 226 may define "certainty" for each state. When the certainty that the female owner is in the state P2 based on the absolute value or the rate of change of the basic body temperature is 70%, and the certainty that the female owner is in the state P2 based on the menstrual cycle is 40%, the physical condition determining unit 226 may determine the certainty of the state P2 based on a simple average or a weighted average of 70% and 40%. Further, when certainty exceeds a predetermined threshold, the physical condition determining unit 226 may comprehensively determine that the female owner is in the state P2.

One or more "consideration timings" are set in accordance with the menstrual cycle. A consideration timing may be a timing at which there is a state shift from a certain state to another state, or may be a timing at which a predetermined period elapses after a state shift. Certainty exceeding a predetermined threshold as in the heretofore described example may be set as a consideration timing. A number of consideration timings set, and a setting timing, are arbitrary.

Although details will be described hereafter, a consideration timing is a milestone of a change in the physical condition of a female owner. When a consideration timing is reached, the robot 100 changes a behavioral aspect, thereby realizing conforming behavior in consideration of the physical condition of the female owner. In this way, the physical condition determining unit 226 determines the physical condition of a female owner based on a body temperature cycle.

Figure 7:
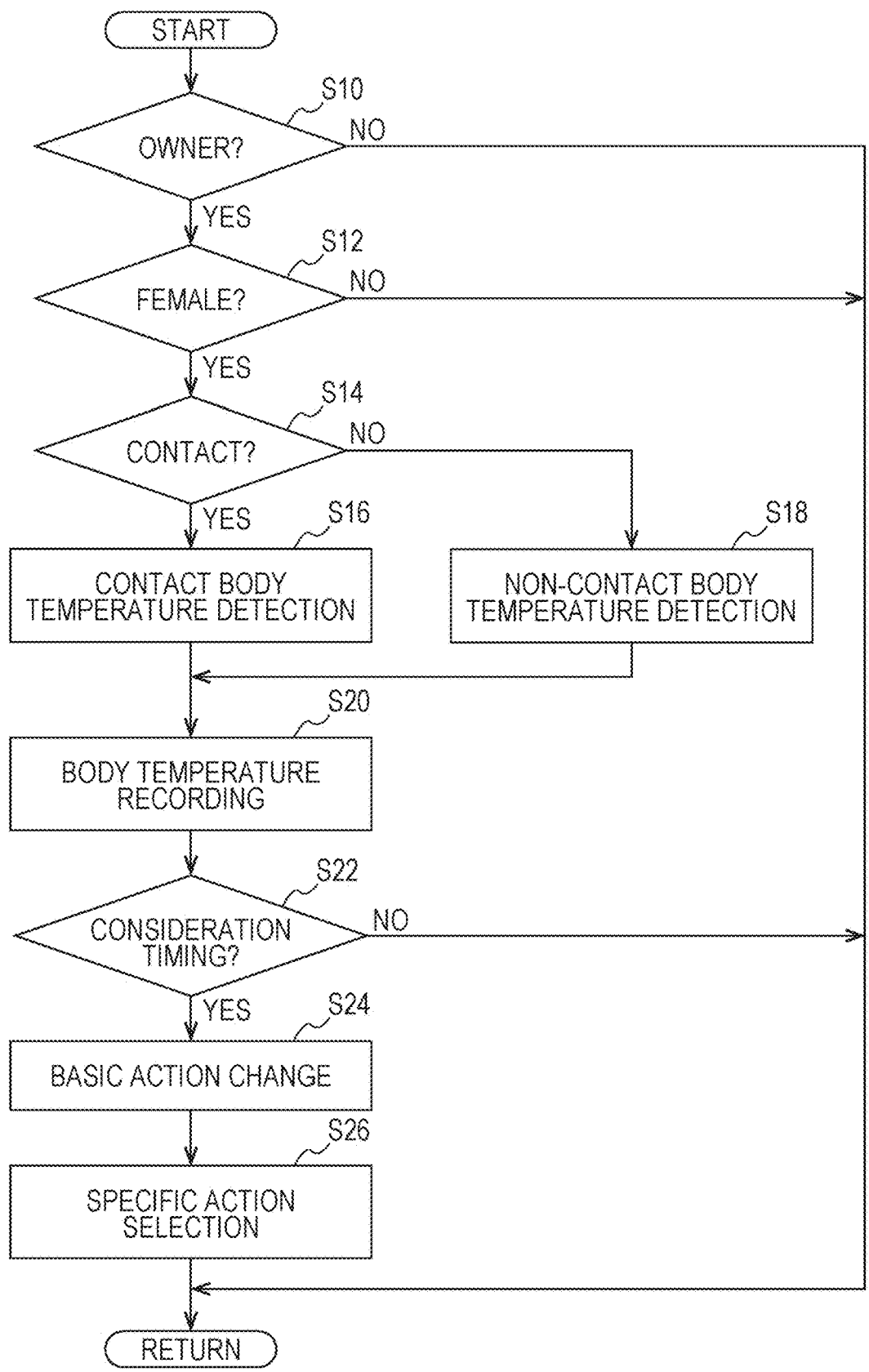
FIG. 7 is a flowchart showing a consideration timing detection process procedure.

FIG. 7 is a flowchart showing a consideration timing detection process procedure.

The detection process shown in FIG. 7 is regularly executed by the robot 100 and the server 200. When the robot 100 detects a person using the camera or the like, the person recognizing unit 214 of the server 200 determines whether or not the person is a female owner (S10, S12). When the person is not an owner (N in S10), or not a female (N in S12), a subsequent process is skipped. Recognition of a female owner is based on user identification using the heretofore described deep learning.

When the person is an owner (Y in S10) and a female (Y in S12), the robot 100 detects the body temperature of the female owner. When the robot 100 and the female owner come into contact (Y in S14), the body temperature is detected by the proximity detection unit 158 (S16). When the robot 100 and the female owner do not come into contact (N in S14), the body temperature is detected by the remote detection unit 154 (S18).

That is, when the robot 100 and the female owner come into contact, the body temperature is detected by the proximity detection unit 158, which has high detection accuracy, and when the robot 100 and the female owner do not come into contact, the body temperature is detected by the remote detection unit 154. In this way, the body temperature can be detected with high accuracy by the proximity detection unit 158 when there is contact, while the body temperature is regularly measured without interruption.

The robot 100 transmits the measured body temperature to the server 200. The physical condition determining unit 226 of the server 200 records the body temperature in the individual data storage unit 218 (S20).

The physical condition determining unit 226 determines whether or not a preset consideration timing has been reached (S22). When a consideration timing has been reached (Y in S22), the operation determining unit 150 changes a basic action (S24), and selects a specific action (S26). When a consideration timing has not been reached (N in S22), a subsequent process is skipped.

Actions of the robot 100 are broadly divided into basic actions and specific actions. A "basic action" is a normal movement of the robot 100. When a consideration timing is reached, the operation determining unit 150 changes the basic action of the robot 100 using a method to be described hereafter in connection with FIG. 8. A "specific action" is a special action defined as an action showing consideration toward an owner. A specific action will be described hereafter in connection with FIG. 9.

A consideration timing that is a trigger for changing a basic action and a consideration timing that is a trigger for executing a specific action do not need to be the same. A setting can also be such that a basic action is changed at a consideration timing 1, a specific action is executed at a consideration timing 2, and a basic action is changed and a specific action executed at a consideration timing 3.

The body temperature of a female owner is desirably detected as the basic body temperature, that is, the body temperature at a time of repose. The robot 100 may measure the body temperature in a time band in which the possibility of the female owner being at rest is high, such as a time when the female owner goes to bed or a time when the female owner gets up. Alternatively, the robot 100 may measure the body temperature when a predetermined time elapses from the female owner sitting down.

Figures 8, 9:
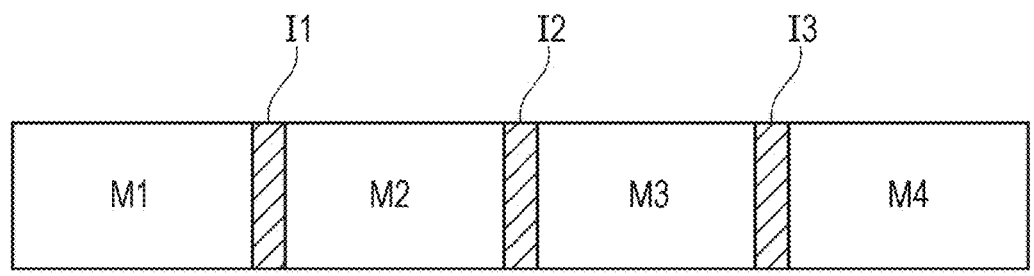
FIG. 8 is a schematic diagram for describing a basic action configured as a compound operation.
FIG. 9 is a data structure diagram of a specific action selection table.

FIG. 8 is a schematic diagram for describing a basic action configured as a compound operation.

Many basic actions of the robot 100 are configured as compound operations that include a multiple of unit operations. FIG. 8 shows a basic action (compound operation) including four motions (unit operations), those being motions M1 to M4. For example, when the robot 100 approaches an owner, the motion M1 may be a unit operation of approaching directly, the motion M2 a unit operation of approaching while raising an arm, the motion M3 a unit operation of approaching while shaking the body, and the motion M4 a unit operation of sitting while raising both arms. By combining these kinds of four motions, a basic operation of "approaching an owner, raising one arm on the way, and finally sitting after shaking the body" is realized. A motion file wherein various basic operations are defined is held in the data storage unit 148 of the robot 100. Motor control information such as an angle of rotation and angular velocity of a motor provided in the robot 100 is defined correlated to a time axis in each motion file. Various actions (movements and gestures) are expressed by each motor being controlled together with the passing of time in accordance with the motor control information.

A motion is an operation including one or both of a selection of a movement by the movement determining unit 138 and a selection of a gesture by the action determining unit 140. Consequently, a "basic action" and a "specific action" include one or both of a movement and a gesture.

Intervals I1 to I3 are provided between motions. An interval is a shift time for changing from a preceding motion to a subsequent motion. It is sufficient that an interval is defined in accordance with time needed for a motion change or details of a motion.

When a consideration timing is reached, the operation determining unit 150 changes a basic action. Specifically, this is an elimination, an addition, or a replacement of a motion, a change of the angle of rotation or a change of the angular velocity of the motor during a motion, or a change of an interval time. For example, "hesitation" may be created in a motion by lengthening the interval time, thereby expressing a cautious action of the robot 100, or a brisk action of the robot 100 may be expressed by shortening the interval. A reserved movement may be expressed by reducing the angle of rotation of the motor.

As one example, a description will be given of a basic action such that the robot 100 approaches a female owner from afar, and asks for a hug. In the state P2, in which the physical condition of the female owner is good, the robot 100 dashes straight to the female owner, sits down near the female owner, and raises both arms asking for a hug. In the state P4, in which the female owner is likely to be irritable and uneasy, the robot 100 winds its way slowly toward the female owner, sits down in a place slightly apart from the female owner, and watches the female owner closely without actively asking for a hug.

In the heretofore described example, the motion of "approaching directly" is replaced by the motion of "approaching while winding". Although a new motion of watching the female owner closely is added, the motion of raising both hands asking for a hug is eliminated. Speed when approaching may be reduced, or the interval time may be changed.

In this way, when a consideration timing is reached, the robot 100 synchronizes a change in the physical condition of a female owner and a behavioral change of the robot 100 by changing an operational amount (operating speed or operation details) of the robot 100. The female owner can recognize that the robot 100 might be adjusting to her in its own way by the behavior of the robot 100 changing in accordance with the physical condition of the female owner.

FIG. 9 is a data structure diagram of a specific action selection table 240.

The specific action selection table 240 defines a specific action that should be executed at a consideration timing. When a consideration timing is reached, the robot 100 selects one or more specific actions from multiple kinds of specific actions. The specific action selection table 240 is stored in the operation pattern storage unit 224 of the robot 100. When referring to FIG. 9, specific actions X1 to Xn are correlated to the consideration timing P1, and a selection probability is correlated to each of the specific actions X1 to Xn. When the consideration timing P1 is reached, the operation determining unit 150 selects the specific action X1 with a 4% probability, and selects the specific action X2 with a 7% probability.

There are various specific actions, from an easy action of simply watching an owner closely, to a complex action of moving away from an owner, stopping on the way, looking back, watching closely, and continuing to move away. What kind of specific action is defined is arbitrary. A specific action may be equivalent to a basic action, or may be a special action not included in basic actions.

A basic action is an action selected regularly or randomly. A specific action is a dedicated action executed when a consideration timing is detected. A specific action may also be a simple action configured of one motion, or may be a compound operation configured of multiple motions.

Not only body temperature, but also a vital sign other than body temperature may be included in a consideration timing determination condition. When detecting body temperature, the expression recognizing unit 230 may detect an expression and a complexion of a female owner. When a smile is detected even though a female owner is in the state P4, in which she is liable to become negative, the physical condition determining unit 226 need not acknowledge this as a consideration timing. The physical condition determining unit 226 recognizes a time when a female owner is in the state P4 according to basic body temperature information, and displays a negative expression such as unease or anger, as a consideration timing, and at this time, the operation determining unit 150 may cause a specific action to be executed.

Figure 10:
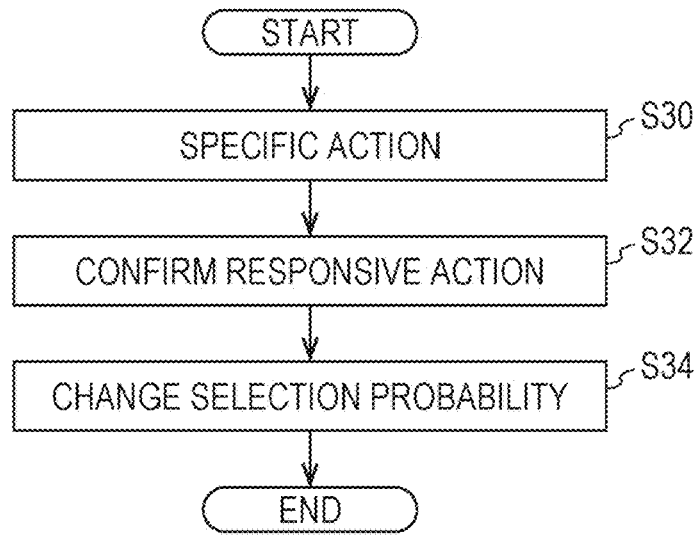
FIG. 10 is a flowchart showing a specific action correction process procedure.

FIG. 10 is a flowchart showing a specific action correction process procedure.

The robot 100 executes a specific action selected by the operation determining unit 150 (S30). After the specific action is executed, the response recognizing unit 228 of the server 200 recognizes a responsive action of a female user (S32). A responsive action is thought to indicate a state of mind of a female user with respect to a specific action of the robot 100. As heretofore described, responsive actions are classified into positive reactions and negative reactions. A positive reaction may be an explicit action such as hugging, touching a specific place (the head or the tip of the nose) on the robot 100, or saying positive words such as "you're cute" or "thank you", or may be an implicit action such as a smile. A negative reaction may also be an explicit action such as kicking, hitting, or saying negative words such as "go away", or may be an implicit action such as displaying a strange expression, being unresponsive, or sighing. The operation determining unit 150 changes the selection probability of the specific action selection table 240 in accordance with a responsive action (S34).

For example, when the specific action X1 is selected at the consideration timing P1, the operation determining unit 150 increases the selection probability of the specific action X1 at the consideration timing P1 from 4% to 5% when a female user shows a positive reaction. By doing so, the robot 100 can learn a specific action that is liked by the female user.

Heretofore, the robot 100, and the robot system 300 including the robot 100, have been described based on an embodiment.

Action selection that cannot be patterned using one or more action maps, is difficult to predict, and is animal-like, is expressed. Using this kind of method, animal-like action selection is emulated.

Normally, when a free and uninhibited pet shows consideration toward a person, affection of the person toward the pet is easily aroused. The robot 100 in this embodiment too, while normally acting instinctively in accordance with an action map, shows consideration, clumsy though it may be, when a consideration timing is detected, because of which affection of an owner toward the robot 100 can be aroused. A prerequisite of consideration is an ability to infer a physical condition as a physical and mental state of an owner. The robot 100 (robot system 300) in this embodiment is such that accuracy of estimating a timing at which consideration should be shown, or in other words, of "ability to read the atmosphere", is increased by referring to a menstrual cycle of a female.

When a consideration timing is reached, the robot 100 changes a basic action. A change of a basic action may be a clear change that a female owner can consciously recognize, or may be a change of an extent that is difficult to recognize consciously but a difference can be subconsciously felt. Even without the robot 100 doing anything special, a female owner can more easily build a rapport (state of mental harmony) with the robot 100 by the robot 100 subtly changing an action in accordance with the physical condition of the female owner, synchronizing the physical condition of the female owner and the action of the robot 100.

A method of managing a user's health by regularly checking the body temperature of the user is commonplace. A robot of JP-A-2001-246580 also helps a person by carrying out a body temperature measurement as an extension of health management. As opposed to this, the robot 100 in this embodiment can provide solace by causing a user to feel that "this little thing understands me", rather than creating a sense of security such as "dependability". Rather than being an information intermediary that relays a cyclical change in physical condition, such as menstruation, to a third person, it is sufficient that the robot 100 quietly shares (is thought to share) a private physical condition problem held by a female owner.

Although a change of a basic action can be said to be a passive consideration, an execution of a specific action is an active consideration. The robot 100 may curry favor with a female owner via an active response such as clinging, watching closely, or moving away while looking back, based on an evaluation of the physical condition of the female owner.

The invention not being limited to the heretofore described at least one embodiment or a modified example, components can be changed or embodied without departing from the scope of the disclosure. Various implementations may be formed by a multiple of the components disclosed in the heretofore described at least one embodiment or the modified example being combined as appropriate. Also, some components may be eliminated from the total of components shown in the heretofore described at least one embodiment or the modified example.

Although a description has been given assuming that the robot system 300 is configured of one robot 100, one server 200, and the multiple of external sensors 114, one portion of the functions of the robot 100 may be realized by the server 200, and one portion or all of the functions of the server 200 may be allocated to the robot 100. One server 200 may control a multiple of the robot 100, or a multiple of the server 200 may control one or more of the robot 100 in cooperation.

A third device other than the robot 100 and the server 200 may manage one portion of functions. A collection of the functions of the robot 100 and the functions of the server 200 described in FIG. 5 can also be comprehensively grasped as one "information processing device". In at least one embodiment, a method of distributing the multiple of functions needed in order to realize the invention with respect to one or multiple items of hardware is determined with consideration to the processing capability of each item of hardware, specifications required of the robot system 300, and the like.

"The robot in a narrow sense" is the robot 100 excluding the server 200, but "the robot in a wide sense" is the robot system 300. It is thought that there is a possibility of many functions of the server 200 being integrated in the robot 100 in future.

For example, in this embodiment, the physical condition determining unit 226 has been described as being one portion of the server 200, but the physical condition determining unit 226 may be a function of the robot 100, or the function may be divided between the robot 100 and the server 200.

As a method of changing a basic action, reducing a volume and pitch of a call or the like, comprehensively reducing a speed of executing a basic action, cutting out a complex motion and adopting a simple movement, and the like are conceivable when a female owner is irritable. In the state P4, which is a period in which a female owner is irritable, a condition determination wherein, when approaching the female owner, the robot 100 carries out expression recognition after approaching to a certain distance, and selects whether or not to approach further in accordance with the expression, may be added. For example, having approached to the certain distance, the robot 100 may refrain from approaching further when a smile of the owner cannot be detected, and approach as far as coming into contact with the owner when a smile can be confirmed. Meanwhile, in the state P1, in which a female owner is likely to be depressed, the robot 100 may increase the frequency of an approaching action.

In addition to this, the robot 100 may sit quietly ensconced near a female owner, rather than asking for a hug, in the state P4, and may set a time of watching a female owner closely to be longer than when in another state in the state P3. In order not to be a source of stress to a female owner, a user other than the female owner may be more easily set as a target point, or a child who is likely to be a source of stress may be more easily set as a target point. When told to "come here" by a multiple of owners, a setting may be changed so as to obey an order from a female owner with priority. There are various ways of showing consideration.

Also, when the physical condition of a female owner is good, as in the state P2, an active basic action such as clinging or asking for a hug may be executed with high frequency, or a setting may be changed to a brisk basic action.

An action actively showing consideration, taking the physical condition of an owner into account, is a specific action. When the physical condition of a female owner is good, as in the state P2, the robot 100 may perform a playful action, such as lightly bumping against the female owner. In a period in which a female owner is irritable or uneasy, as in the state P4, a specific action such as moving away from the female owner and watching closely may be executed.

There is a possibility that the basic body temperature of a female owner can be measured with higher accuracy by the proximity detection unit 158 than by the remote detection unit 154. Meanwhile, measurement with the proximity detection unit 158 can only be carried out when the proximity detection unit 158 is in contact with a female owner. When it is determined as a result of measuring body temperature with the remote detection unit 154 that a consideration timing has been reached, the physical condition determining unit 226 may instruct the operation determining unit 150 to confirm the body temperature. At this time, the operation determining unit 150 executes an action of approaching the female owner, and for the sake of confirmation, attempts a high accuracy body temperature detection using the proximity detection unit 158.

According to this kind of control method, highly accurate body temperature detection using the proximity detection unit 158 can be carried out at an appropriate timing, without relying only on the remote detection unit 154, because of which consideration timing detection accuracy can easily be increased.

When the remote detection unit 154 detects the body temperature of a female owner, a point forming a measurement target may be defined in advance. For example, a place with a high possibility of being exposed, such as a cheek or the back of a hand, may be set as a measurement point. The body temperature may be measured at a multiple of measurement points, such as a cheek, the back of a hand (two places), and an ankle (two places), and an average value thereof may be taken as the body temperature of the female owner. A case in which the body temperature can only be obtained at one portion of measurement points among the multiple of measurement points may be taken as being invalid, and a case in which measurement can be carried out at a predetermined number or more of measurement points, for example, a total of three places—a cheek and the back of a hand (two places)—or more, may be taken as a valid measurement.

Alternatively, places on the body of a female owner that are of a predetermined temperature (for example, 30 degrees) or higher may be taken to be exposed places, and an average value of body temperatures in the exposed places may be taken as the body temperature of the female owner.

In the same way, when a predetermined time elapses after a body temperature detection by the proximity detection unit 158, the physical condition determining unit 226 may instruct the operation determining unit 150 to confirm the body temperature. For example, when eight hours elapse after a body temperature detection by the proximity detection unit 158, the physical condition determining unit 226 instructs the operation determining unit 150 to confirm the body temperature. The operation determining unit 150 may execute an approaching action at an arbitrary timing within three hours of receiving the instruction to confirm the body temperature, for example, a timing at which the female owner is in a state of repose, and the body temperature may be detected by the proximity detection unit 158.

According to this kind of control method too, highly accurate body temperature detection using the proximity detection unit 158 can be carried out successively, without relying only on the remote detection unit 154, because of which consideration timing detection accuracy can easily be increased.

In this embodiment, it has been described that mainly the recognizing unit 156 of the robot 100 detects a user via the internal sensor 128, but the recognizing unit 212 of the server 200 may also detect the existence of a user via the external sensor 114. The external sensor 114 may also incorporate a smell sensor and a highly directional microphone. In particular, even when detection accuracy of the internal sensor 128 is insufficient with respect to sound and smell, detection accuracy can be increased by the internal sensor 128 being used in combination with the external sensor 114. Also, when capturing a user too, characteristics are more easily extracted by the same user being captured from a different angle by a camera incorporated in the external sensor 114, rather than using only the incorporated camera acting as the internal sensor 128.

In this embodiment, it has been described that the robot 100 films various users, also acquires other data such as smell, speech, and body temperature when filming, carries out an extraction of characteristics from these items of data, and identifies (clusters) a multiple of users by carrying out cluster analysis.

As a modified example, a user may set the physical characteristics and the behavioral characteristics of each user in the server 200 in advance. For example, as characteristics of the father, information such as having a beard, getting up early, being 170 centimeters tall, and being a smoker may be provided as teacher data to the individual data storage unit 218 of the server 200. Based on these items of characteristic information, the server 200 may carry out user detection using an already known method, such as deep learning.

As easier user recognition means, the robot 100 may identify a user by regularly receiving user ID from a mobile device such as a smartphone possessed by the user. With regard to a pet too, easy identification can be carried out by attaching a radio frequency identifier (RFID) tag to a collar. According to this kind of control method, the processing burden of the robot 100 and the server 200 can be considerably reduced.

A user detected within a predetermined time from first turning on power to the robot 100 may be recognized as being a family member. At this time, the robot 100 may be taught which user is female.

In this embodiment, a specific action selection algorithm is changed in accordance with whether a responsive action of a female owner in response to a specific action is a positive reaction or a negative reaction. In the same way, a basic action may also be changed based on a responsive action of a female owner. For example, when a female owner smiles when approached in response to a basic action of stopping once when approaching the female owner, the basic action may be corrected to a basic action of approaching without stopping.

A change of a basic action is not limited to a change with respect to a female owner. For a male owner too, it is sufficient that a basic action is changed in accordance with a responsive action of the owner. A basic action selection algorithm may be changed for each owner.

In this embodiment, a description has been given of the robot 100 that focuses on the connection between the menstrual cycle and the physical condition of a female owner, and shows consideration toward the female owner. As a modified example, application to attempts to conceive, or the like, is conceivable by the robot 100 relaying a menstrual cycle to a third person in accordance with a behavioral aspect of the menstrual cycle.

A comprehensive determination of a consideration timing may be carried out including not only basic body temperature, but also a vital sign other than basic body temperature. For example, the skin of a female user may be filmed in close-up at the timing of S16 of FIG. 7, and one of the states P1 to P4 may be determined from a degree of skin roughness. In order to do this, the recognizing unit 212 of FIG. 5 may further include a skin state determining unit (not shown) that determines the state of the skin by carrying out an imaging process on a close-up image of the skin. A more accurate state determination can be carried out by combining the basic body temperature and skin state information. The robot 100 may perform a gesture asking for a hug in order to be able to film a close-up image of the skin of a female user, or may perform a gesture prompting a change in orientation of a hug so that a close-up imaging camera faces the skin of a female user.

In addition to this, a smell determination may be carried out in S16 of FIG. 7. As a smell of a female changes in accordance with the menstrual cycle, combining with a smell determination is also conceivable. The consideration timing detection accuracy can be increased by creating a smell category corresponding to each of the states P1 to P4, and determining which category a smell detected by the smell sensor fits into.

In addition to this, physical condition may be determined from a direct utterance such as "it's my time of the month", or from an utterance suggesting a physical condition, such as "I'm tired", "I feel lethargic", or "that's lucky". The expression recognizing unit 230 may determine the physical condition of an owner by recognizing the expression or the complexion of the owner.

A consideration timing may be sought by an action. In a case of a female owner who dislikes a lively action of the robot 100, for example, an action of moving around at high speed, when she is in the state P2, the robot 100 deliberately executes that kind of action, and observes a responsive action of the female owner. When the responsive action is a negative reaction, the robot 100 can recognize that the female owner is in the state P2.

When defining "certainty" for each state, the physical condition determining unit 226 may change basic actions that can be selected as certainty increases with respect to a certain state. For example, when the certainty with respect to the state P2 is 60%, a basic action E of basic actions A to E may be excluded as an execution target, and when the certainty exceeds 70%, the basic action D may also be excluded as an execution target. In this way, the physical condition of an owner and an action of the robot 100 may be synchronized by increasing or reducing the kinds of basic action or specific action that can be selected in accordance with the body temperature cycle.

Rather than determining which of the states P1 to P4 a female owner is in by categorizing, a condition of the owner may be calculated from basic body temperature, smell, expression, and the like. Provisionally, condition is expressed by the numerals 1 to 100. 100 is a best condition, and 1 is a worst condition. It is taken that the state P1 is 20, the state P2 is 80, the state P3 is 50, and the state P4 is 40. 10 may be added to the condition when a laughing voice or a smile is recognized, 20 may be deducted from the condition when a crying voice or a crying face is recognized, and 10 may be deducted from the condition when a sigh is detected by speech detection. Further, a time at which the condition reaches a predetermined value may be set as a consideration timing. Although the above is one example, it is sufficient that the condition of an owner is estimated by combining various vital signs such as body temperature cycle and expression, and an action of the robot 100 may be changed in accordance with the condition.

To summarize, it is sufficient that the robot 100 selects an action based on vital signs of an owner, without being limited to basic body temperature information. The body temperature cycle is information that is useful in determining the physical condition of an owner, but even in the state P2, in which physical condition is generally assumed to be good, it is not necessarily the case that physical condition is actually good. Even when a female owner is in the state P2, the robot 100 may select an action that takes a poor condition of the owner into consideration when the complexion is bad, the expression is severe, or a negative utterance or a sigh is detected. By selecting an action based on vital signs of an owner without being limited to the basic body temperature, the robot 100 can perform an act that takes the physical condition of the owner into consideration, even in various cases such as menstrual irregularity, pregnancy, a breast feeding period, and pre-menopause. Also, the robot 100 can perform an act that takes the physical condition of a female owner into consideration, even when there is no record of the basic body temperature of the female owner.

Figure 11:
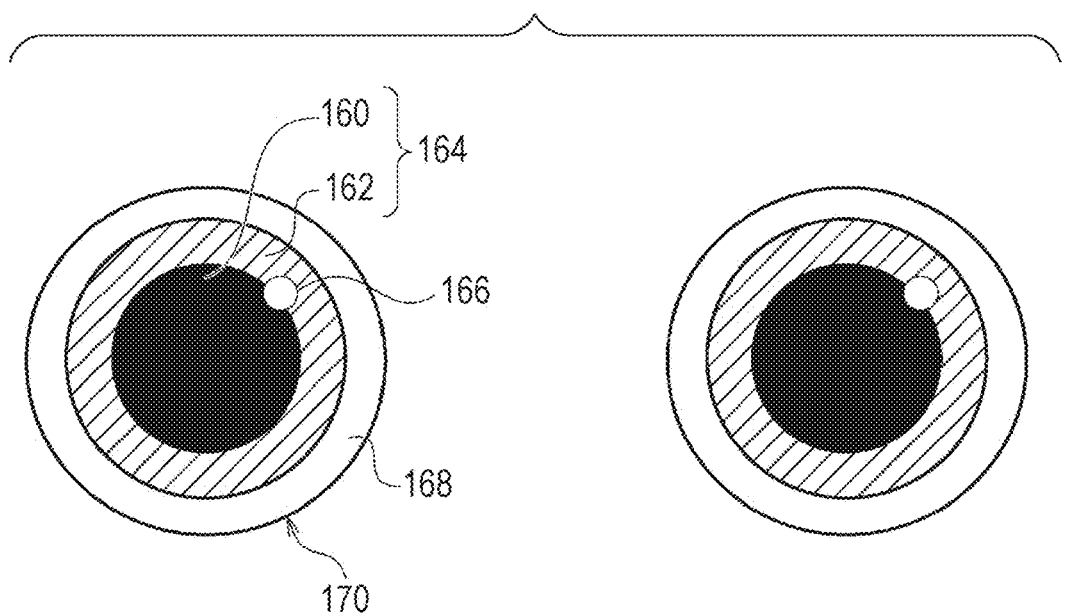
FIG. 11 is an external view of an eye image in a first modified example.

FIG. 11 is an external view of an eye image 174.

As a first modified example, the data processing unit 136 of the robot 100 may include an eye generating unit and an eye display unit. In this case, the eye 110 of the robot 100 is formed as a display on which the eye image 174 is displayed.

The eye generating unit generates the eye image 174 including a pupil image 164 and a peripheral edge image 168. The eye generating unit causes the eye image 174 to be displayed as a moving image. Specifically, the line of sight of the robot 100 is expressed by moving the pupil image 164. Also, a blinking operation is executed at a predetermined timing. The eye generating unit expresses a large variety of movements of the eye image 174 in accordance with various operation patterns. The eye display unit causes the eye image 174 to be displayed on a monitor of the eye 110. The monitor desirably has a curved surface form, in the same way as a human eyeball.

The pupil image 164 includes a pupillary region 160 and a corneal region 162. Also, a catch light 166 for expressing a reflection of external light is also displayed in the pupil image 164. Rather than shining owing to a reflection of external light, the catch light 166 of the eye image 174 is an image region expressed as a high-luminance region by the eye generating unit.

The eye generating unit can move the pupil image 164 vertically and horizontally on the monitor. When the recognizing unit 156 of the robot 100 recognizes a moving object, the eye generating unit generates an operation pattern (moving image data) such that the pupil image 164 is oriented in the direction in which the moving object exists. The eye display unit can express a "gaze" of the robot 100 by causing the display of the eye image 174 to change in accordance with the operation pattern.

When a consideration timing is reached, the eye display unit may change the display aspect of the eye image 174. For example, a shape of the catch light 166 may be changed to a heart shape, or a size or color of the pupillary region 160 may be changed. In this way, the eye display unit (consideration display unit) may display the matter that reaching a consideration timing has been recognized, or that an accompanying specific action (consideration action) is being executed, in the eye image 174. The eye display unit may directly display the matter that consideration is being shown as character information in the eye 110. In a modified example, a consideration display unit formed as an eye display unit may display image information or character information indicating that consideration is being shown, not only in the eye 110, but also in another display device included in the robot 100. When a consideration timing is reached, the consideration display unit notifies an external device, for example the server 200, of the matter, and the external device may cause the matter that a consideration action is being performed to be displayed as an image.

Not being limited to when a consideration timing is reached, a report trigger can be set arbitrarily to a user being in a predetermined state, for example, a user being in the state P4, certainty of a user being in the state P4 being of a predetermined value or greater, or the like.

FIG. 12 is a data structure diagram of an action selection table 250 in a second modified example.

Hereafter, settings involved in controlling an action of the robot 100, such as which motion is chosen and when, and output regulation of each actuator when realizing a motion, will collectively be called "action properties". The action properties of the robot 100 are defined by a motion selection algorithm, a motion selection probability, a motion file, and the like.

The operation determining unit 150 of the robot 100 refers to the action selection table 250, and selects an action (hereafter called a "response action") in accordance with each kind of event. An event in this case can be defined arbitrarily as, for example, a user not getting out of bed even though morning has come, a user looking to be in a bad mood, or the like. The action selection table 250 is stored in the operation pattern storage unit 224 of the robot 100. When referring to FIG. 12, response actions Y1 to Ym are correlated to an event E1, and a selection probability is correlated to each of the response actions Y1 to Ym. When the event E1 occurs when the user is in the state P1, the operation determining unit 150 selects the response action Y1 with a 3% probability, and selects the response action Y2 with a 2% probability. Meanwhile, when the event E2 occurs in the state P2, the operation determining unit 150 selects the response action Y1 with a 10% probability, and selects the response action Y2 with a 1% probability. When there are a multiple of users, the operation determining unit 150 may select a response action in accordance with the state of the user with the highest familiarity, or may select a response action in accordance with the state of a user to whom consideration should be shown when near the user, and select a usual response action when distanced from the user.

The physical condition determining unit 226 determines which of the states P1 to P4 a user is in. The operation determining unit 150 changes the selection probability of a response action with respect to an event in accordance with the state. According to this kind of control method, the action properties of the robot 100 can be changed in accordance with the state (physical condition) of a user. Because of this, the user can feel that the overall behavior of the robot 100 changes in accordance with the user's physical condition. "Consideration" can be shown subtly by causing the action properties of the robot 100, particularly a response action with respect to an event, to change together with a change in the physical condition of a user. For example, even in a case of the robot 100 that, when a ball is rolling in the living room, displays a response action of chasing the ball with a high probability, the selection probability of the response action of chasing the ball may be restricted when a user is in the state P4, is asleep, or has a fever.

FIG. 13 is a data structure diagram of an action selection table 260 in a third modified example.

In the third modified example, the robot 100 carries out an action selection in accordance with the category and the physical condition of a user. The person recognizing unit 214 determines user attributes such as an age group and gender of a user from facial image information of the user, using already known image recognizing technology. The action selection table 260 shown in FIG. 13 defines an action in accordance with the physical condition of a user when the user is a male child. When referring to FIG. 13, the operation determining unit 150 selects an action Z1 with a 2% probability, and selects an action Z2 with a 1.2% probability, when the physical condition of the male child is in a state C1. Meanwhile, when the physical condition is in a state C2, the operation determining unit 150 selects the action Z1 with a 3.2% probability, and selects the action Z2 with a 4% probability.

The physical condition determining unit 226 carries out a recognition of a state such as looking to be in a bad mood or having a fever using image recognition and temperature recognition, and classifies the physical condition of the user into a multiple of categories such as "in good condition", "in bad condition", "has a fever", "feeling lethargic", and "in a bad mood". For example, the physical condition determining unit 226 may track the behavior of a user P1, and determine a time for which the user P1 is asleep by detecting a time at which the user P1 goes to bed and a time at which the user P1 gets up. When the time for which the user P1 is asleep is equal to or less than a predetermined time, and the user P1 displays a displeased expression, the physical condition determining unit 226 determines that the user P1 is in a state of being in a bad mood (a first physical condition) due to a lack of sleep. At this time, by setting so that the selection probability of an action of approaching the user P1 is low, the robot 100 can express by behavior a refraining from action in consideration of the user P1, who is in a bad mood.

Also, the action selection table 260 may be set so that when a user P2 has a fever, the selection probability of an action of approaching and watching over the user P2 is high.

The action selection table 260 is defined so that action selection changes in accordance not only with the physical condition, but also the category of a user. For example, when an elderly female has a fever, the robot 100 may select an action of sitting near the user and watching closely with a high probability, and when a male child has a fever, the robot 100 may refrain from an action of approaching the male child in order not to excite the male child. In this way, a consideration action in accordance with a condition of a user can be performed by changing the action properties in accordance with not only the physical condition of the user, but also attributes of the user. Also, in addition to operation selection, the operating speed of the robot 100 may be restricted by a process such as reducing movement speed or reducing actuator drive speed when a male child has a fever.

When the robot 100 is to approach to a distance at which the robot 100 can be touched by a user (a first distance), the action determining unit 140 may cause the robot 100 to perform a gesture of stopping once and watching the user closely before reaching a final approach point, at a distance at which the user can be aware of the robot 100 and at which the user cannot be touched (a second distance longer than the first distance). In this way, by adding an action that causes hesitation to be noticed in a series of actions that are executed continuously at a normal time, the robot 100 expresses an aspect of understanding a poor physical condition of a user, worrying, and showing consideration. Also, at this time, the recognizing unit 156 may acquire a facial image of the user, and the expression recognizing unit 230 may confirm the expression of the user from the facial image. The expression recognizing unit 230 classifies the expression of the user using already known expression recognition technology. When the expression of the user is classified into a category correlated to "displeased", the movement determining unit 138 stops an operation of approaching the user. Alternatively, the movement determining unit 138 may select a direction of movement so that the robot 100 moves away from the user after the approach to the user is stopped. Even when the expression of the user is classified into the heretofore described category, the movement determining unit 138 may cause the approach to the user to be continued when the user exhibits predetermined behavior allowing an approach. Behavior allowing an approach in this case is, for example, the user displaying a smile (after a displeased expression), emitting an utterance allowing an approach, such as "come here" (uttering a term of affection or the like), performing a gesture allowing an approach, such as beckoning with a hand, or the like.

During a specific action, the exterior may be notified using an image or a signal that the specific operation is being executed, as heretofore described. Also, when a specific action is being executed, the matter that the specific action is being executed, or in other words, the matter that consideration is being shown, may be suggested by action or gesture by, for example, including a unit operation such as waving the arm 106 as one portion of a compound operation. The operation determining unit 150 may carry out this kind of operation change even when a user is in a predetermined state, such as the state P4.

As heretofore described, the robot 100 may change the selection probability of a response action with respect to an event in accordance with the physical condition of a user.

Also, the robot 100 may change the action properties in accordance with the physical condition of a user, regardless of an event. For example, the data processing unit 202 of the server 200 may include a history recording unit that records a history of actions of the robot 100 selected by the operation determining unit 150. Further, when a user is in the state P4, the operation determining unit 150 may express "action properties different from usual" by selecting an "operation not usually performed" of a selection probability of a predetermined value or lower in the action history with a probability of the predetermined value or higher, or by selecting an "often performed operation" of a selection probability of a predetermined value or higher with a probability of the predetermined value or lower.

For example, the operation determining unit 150 of the robot 100 may cause the robot 100 to execute a routine action of completing three circuits of the living room at 8 o'clock in the morning (jogging). However, when a user is in the state P4, the operation determining unit 150 may change the action properties so as to shorten the routine action to one circuit, reduce a rotation radius, reduce the movement speed, or not execute the routine action itself. A change in the action properties can be expressed by not doing something that is usually done.

The physical condition determining unit 226 may calculate the heretofore described certainty based on a parameter other than the absolute value of the basic body temperature or the menstrual cycle. For example, certainty may be added or subtracted when a condition is met for various physical characteristics or behavioral characteristics, such as movement of a user being sluggish, or the user looking to be in a bad mood.

Not being limited to the menstrual cycle, a consideration timing may be correlated to various conditions, such as the body temperature exceeding a predetermined value, or a user looking to be in a bad mood.

When the recognizing unit 212 detects that a user is continuously unmoving for a predetermined time or more, the movement determining unit 138 may instruct an approach to the user, and the body temperature detecting unit 152 may measure the body temperature (basic body temperature) of the user, who is in a state of repose.

When the physical condition determining unit 226 determines that a female owner is in the state P4, the movement determining unit 138 may set a point a predetermined distance away from the female owner as a movement target point, and the action determining unit 140 may instruct the robot 100 to sit down after arriving at the movement target point. Also, when a female owner is in a specific state such as the state P4, the movement determining unit 138 may cause the robot 100 to approach a child that is a source of stress to the female owner, thereby preventing the child from being interested in the female owner. Alternatively, when a room is messy, the movement determining unit 138 may cause the robot 100 to lead the child to the place that is messy, and encourage the child to "clear up" before the female owner gets angry by pointing to the mess with the arm 106.

A response action is managed by correlating to an event in the action selection table 250 in the second modified example described using FIG. 12, but the action selection table 250 may hold a value correlated to each response action indicating an amount of activity involved in the action. Furthermore, an activity amount table in which a value indicating a range of permitted activity amounts is held, correlated to each state determined by the physical condition determining unit 226, is stored in the operation pattern storage unit 224. The operation determining unit 150 may identify a range of activity amounts in accordance with the state of a user determined by the physical condition determining unit 226 by referring to the activity amount table, and select a response action that comes within the range of activity amounts. Because of this, the operation determining unit 150 can select a response action with a high amount of activity when the physical condition of a user is good, and select a response action with an amount of activity lower than that when the physical condition is good when the physical condition of the user is poor.

What is claimed is:

1. An autonomously acting robot, comprising:
   a processor configured to execute instructions for:
      receiving information regarding a body temperature of a user;
      determining a condition of the user based on a cyclical history of the detected body temperature, wherein the condition is selected from a plurality of preset states;
      selecting an operation of the robot based on the determined condition of the user, wherein selecting the operation comprises selecting a preset specific action as the selected operation in response to the determined condition of the user being a predetermined condition; and
   a drive mechanism in communication with the processor, wherein the drive mechanism is configured to execute the selected operation.

2. The autonomously acting robot according to claim 1, wherein the selecting the operation of the robot comprises changing an amount of activity of the robot in response to a change in the determined condition of the user.

3. The autonomously acting robot according to claim 1, wherein the selected operation comprises a compound operation comprising multiple unit operations, and
   the processor is configured to execute the instructions for changing at least one unit operation of the multiple unit operations in response to a change in the determined condition of the user.

4. The autonomously acting robot according to claim 1, wherein the selected operation comprises a compound operation comprising multiple unit operations, and
   the processor is configured to execute the instructions for changing a time taken to shift from a first unit operation of the multiple unit operations a second unit operation of the multiple unit operations in response to a change in the determined condition of the user.

5. The autonomously acting robot according to claim 1, wherein the processor is configured to execute the instructions for instructing a display unit to display a consideration action in response to the determined condition of the user being a predetermined condition.

6. The autonomously acting robot according to claim 1, further comprising a sensor for detecting the body temperature of the user, wherein the sensor comprises a non-contact temperature sensor or a contact temperature sensor.

7. The autonomously acting robot according to claim 6, wherein the processor is configured to execute the instructions for selecting an action of approaching the user as the selected operation in response to a predetermined time elapsing after the body temperature detection by the contact temperature sensor.

8. The autonomously acting robot according to claim 6, wherein the processor is configured to execute the instructions for selecting an action of approaching the user as the selected operation in response to the detected body temperature of the user by the non-contact temperature sensor indicates that the determined condition of the user is a predetermined condition.

9. The autonomously acting robot according to claim 1, wherein the processor is configured to execute the instructions for recognizing an expression of the user from an image, and for determining the condition of the user based on the body temperature and the recognized expression of the user.

10. The autonomously acting robot according to claim 1, wherein the processor is configured to execute the instructions for:
recognizing a responsive action of the user,
selecting any one specific action from multiple kinds of specific actions as the selected operation in response to the determined condition of the user being a predetermined condition,
wherein a selection probability of each of the multiple kinds of specific actions is determined based on the recognized responsive action.

11. The autonomously acting robot according to claim 1, wherein the processor is configured to execute the instructions for:
selecting a response action in response to detection of an event occurs, wherein the detection of the event is based on an action selection table that defines an event, and the response action is selected from a plurality of response actions associated with the event in the action selection table,
wherein selecting of the response action is based on the determined condition of the user.

12. An autonomously acting robot, comprising:
a processor configured to execute instructions for:
receiving information regarding a body temperature of a user;
determining a distance from the autonomously acting robot and the user;
determining a condition of the user based on a cyclical history of the detected body temperature, wherein the condition is selected from a plurality of preset states;
recognizing whether a user reaction is a positive reaction; and
selecting an operation of the robot based on the determined condition of the user, wherein the selecting of the operation comprises selecting moving the autonomously acting robot closer to the user in response to:
the determined condition being a predetermined condition,
the user reaction being the positive reaction, and
the distance being greater than a threshold distance; and
a drive mechanism configured to execute the selected operation.

13. An autonomously acting robot, comprising:
a processor configured to execute instructions for:
recognizing whether a user reaction is a positive reaction;
selecting an operation based on both a detected vital sign of a user and whether the user reaction is the positive reaction; and
a drive mechanism configured to execute the selected operation.

14. The autonomously acting robot according to claim 13, wherein the processor is further configured to execute the instructions for:
determining a physical condition of the user based on the detected vital sign of the user, and
selecting the operation is based on an action selection table that defines a physical condition, and the operation is selected from a plurality of response actions associated with the physical condition in the action selection table,
wherein selecting of the response action is based on the determined physical condition of the user.

15. The autonomously acting robot according to claim 13, wherein the processor is further configured to execute the instructions for:
determining a category of the user,
selecting the operation is based on an action selection table that defines a physical condition, and the operation is selected from a plurality of response actions associated with the physical condition in the action selection table,
wherein selecting of the response action is based on the determined physical condition of the user and the determined category of the user.

16. The autonomously acting robot according to claim 13, wherein the processor is further configured to execute the instructions for:
determining a category of the user,
restricts an operating speed of the robot in response to the category of the user being a child, and the vital sign of the user indicates a fever.

17. The autonomously acting robot according to claim 13, wherein the processor is further configured to execute the instructions for:
determining a physical condition of the user based on the detected vital sign of the user, and
restricting an amount of activity of the robot in response to the determined physical condition determining unit indicating that the user is in poor physical condition.

18. The autonomously acting robot according to claim 13, further comprising a sensor for detecting the body temperature of the user as the vital sign of the user, wherein the sensor comprises a non-contact temperature sensor or a contact temperature sensor.

19. The autonomously acting robot according to claim 13, further comprising a display configured to display information related to the detected vital sign of the user.

20. The autonomously acting robot according to claim 1, further comprising a sensor configured to detect a response to the executed selected action, wherein the processor is configured to adjust a probability of the selected action based on the detected response.

* * * * *